United States Patent
Chedid et al.

(10) Patent No.: US 11,649,280 B2
(45) Date of Patent: May 16, 2023

(54) ANTIBODIES TO IL-34

(71) Applicant: Eli Lilly and Company, Indianapolis, IN (US)

(72) Inventors: Marcio Chedid, Fishers, IN (US); Victor H. Obungu, McCordsville, IN (US); Andrew Dixon Skora, Solana Beach, CA (US); Ming Ye, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 26 days.

(21) Appl. No.: 17/238,549

(22) Filed: Apr. 23, 2021

(65) Prior Publication Data

US 2021/0363232 A1    Nov. 25, 2021

Related U.S. Application Data

(60) Provisional application No. 63/017,748, filed on Apr. 30, 2020.

(51) Int. Cl.
| | | |
|---|---|---|
| *A61K 39/395* | (2006.01) | |
| *C07K 16/24* | (2006.01) | |
| *G01N 33/577* | (2006.01) | |
| *G01N 33/68* | (2006.01) | |
| *A61K 39/00* | (2006.01) | |

(52) U.S. Cl.
CPC ......... *C07K 16/244* (2013.01); *G01N 33/577* (2013.01); *G01N 33/6869* (2013.01); *A61K 2039/505* (2013.01); *C07K 2317/565* (2013.01); *C07K 2317/71* (2013.01); *G01N 2333/54* (2013.01)

(58) Field of Classification Search
CPC ............ G01N 33/577; A61K 2039/505; C07K 2317/565; C07K 2317/76
See application file for complete search history.

(56) References Cited

U.S. PATENT DOCUMENTS 10,703,813 B2    7/2020    Heymann et al.

FOREIGN PATENT DOCUMENTS

| WO | 2013/119716 A1 | 8/2013 |
|---|---|---|
| WO | 2016/016262 A1 | 2/2016 |
| WO | 2016/097420 A1 | 6/2016 |
| WO | 2016/196679 A1 | 12/2016 |
| WO | 2019/169291 A1 | 9/2019 |
| WO | PCT/US2021/028861 | 7/2021 |

OTHER PUBLICATIONS

Zhou et al. Functions of interleukin-34 and its emerging association with rheumatoid arthritis. Immunology, Dec. 2016;149(4):362-373.*

The International Searching Authority, International Search Report, for PCT/US2021/028861, filed Apr. 23, 2021, WO, dated Jul. 30, 2021.

Written Opinion of the International Searching Authority for PCT/US2021/028861, filed Apr. 23, 2021, WO.

Becher, et al, *Cytokine networks in neuroinflammation*, Institute of Experimental Immunology, University of Zurich, Zurich 8057, Switzerland, Department of Immunology, University of Washington, Seattle, Washington, USA, pp. 1-11, 2016.

Felix, et al, Structure and Assembly Mechanism of the Signaling Complex Mediated by Human CSF-1, CellPress, Structure Article, pp. 1621-1636.

Wang, et al, Interkeukin-34, a cytokine crucial for the differentiation and maintenance of tissue resident macrophages and Langerhans cells, Department of Pathology and Immunology, Washington University School of Medicine, St. Louis, MO, USA, Eur J Immunol. Jun. 2014; 44(6) 1575-1581.

* cited by examiner

*Primary Examiner* — Dong Jiang
(74) *Attorney, Agent, or Firm* — Dan L. Wood

(57) ABSTRACT

The present invention relates to IL-34 antibodies, compositions comprising the same, and methods of using the antibodies and or compositions thereof for treating immune-mediated diseases such as neurodegenerative diseases, for example Alzheimer's Disease or a tauopathy disease.

7 Claims, 4 Drawing Sheets

Specification includes a Sequence Listing.

ANTIBODIES TO IL-34

The present invention relates to compounds, pharmaceutical compositions, and methods, which include antibodies directed against human interleukin-34 (IL-34), which are expected to be useful in the field of neuroinflammation and acute or chronic inflammatory diseases. In particular, the embodiments are expected to be useful in treatment and/or diagnostic applications relating to Alzheimer's Disease, as well as other tauopathies.

Alzheimer's disease (AD), a leading cause of dementia, develops in one percent of the population between the ages 65 and 69, and increases to 40-50% in those 95 years and older. AD patients exhibit telltale clinical symptoms that include cognitive impairment and deficits in memory function. In these patients, the presence of AD is confirmed by heavy senile plaque burden and neurofibrillary tangles (NFT) found in the cerebral cortex upon post-mortem histopathological examination. The mature senile plaques consist of extracellular β-amyloid peptides derived from enzymatic processing of amyloid precursor protein and intracellular neurofibrillary tangles (NFT), which are derived from filaments of hyperphosphorylated tau proteins. Aggregates of hyperphosphorylated tau, such as neurofibrillary tangles, are linked to the degree of cognitive impairment in Alzheimer's disease. In AD and various other tauopathies, tau aggregates appear in specific brain regions and patterns that are linked to disease risk, onset, and or progression, and these regions and patterns are known to skilled artisans.

Cytokines regulate normal homeostatic tissue functions, and dysregulation of these cytokine networks is associated with pathological conditions. The central nervous system (CNS), where few blood-borne immune cells circulate, seems to be particularly vulnerable to dysregulated cytokine networks. In neurodegenerative diseases, CNS-resident cells are the predominant producers of pro-inflammatory cytokines and can contribute to dysregulated cytokine networks and neuroinflammation. Damage to the CNS may involve recruitment of circulating immune cells resulting in an innate immune response consisting of resident microglia, peripherally derived monocytes, macrophages and dendritic cells. The activation states of microglia and macrophages are not strictly pro or anti-inflammatory and instead may have a spectrum of functional states. Microglia and/or peripherally derived monocytes and macrophages may acquire an anti-inflammatory phenotype, in which they remove debris and promote regeneration and homeostasis. Neuronal dysfunction or damage can also activate microglia to produce pro-inflammatory cytokines and recruit leukocytes from the bloodstream. In neurodegenerative conditions, such as Alzheimer's disease (AD), microglia activation is a frequent finding and reflects the tissue response to accumulation of extracellular beta-amyloid plaques and hyperphosphorylated tau aggregates. Neuroinflammation is an important component of neurodegenerative diseases and is characterized by elevated production of pro-inflammatory cytokines by CNS cells (Becher, B., Spath, S. & Goverman, J. *Cytokine networks in neuroinflammation*. Nat Rev Immunol 17, 49-59 (2017)). Neuroinflammation and microgliosis are believed to be mechanisms underlying neurodegenerative diseases such as plaque accumulation in Alzheimer's disease, and neuronal death and dysfunction in Parkinson's disease and Huntington's disease.

Microgliosis involves the abnormal proliferation and/or hypertrophy of microglia in response to inflammatory signals. Broadly, IL-34 acts as a potent and pleiotropic cytokine in the regulation of inflammatory and immune processes and is a key regulatory cytokine for the growth of CNS-resident microglia in normal tissue homeostasis. IL-34 is expressed by neurons in the cortex, the anterior olfactory nucleus and the hippocampus. IL-34 is closely related to colony-stimulating factor 1 (CSF1; also known as M-CSF), and both cytokines bind the CSF1 receptor. IL-34 is a secreted homodimeric cytokine that acts as one of two activating ligands for CSF1R, and triggers receptor autophosphorylation and dimerization with subsequent activation of multiple signaling pathways (See, for example, *Structural basis for the dual recognition of helical cytokines IL-34 and CSF-1 by CSF-JR*. Structure 20, 676-687, and Felix J, De Munck S, Verstraete K, Meuris L, Callewaert N, Elegheert J. et al.). Human and mouse IL-34 polypeptides are disclosed for example in U.S. Pat. No. 9,770,486. IL-34 is a protein of 242 amino acids in humans (SEQ ID NO: 41), and 235 amino acids in mouse (SEQ ID NO: 42).

Anti-IL-34 antibodies have been described in the art, and for example, WO 2016/196679 recites various anti-IL-34 antibodies and potential uses thereof. However, to date, no antibody targeting IL-34 has been approved for therapeutic use.

Thus, there remains an unmet need for alternative and/or improved anti-IL-34 antibodies, pharmaceutical compositions thereof, and methods of using the same for therapeutic and/or in diagnostic applications relating to immune-mediated diseases involving IL-34, and/or diseases treatable with an anti-IL-34 antibody, such as neuroinflammatory disorders, and/or Alzheimer's Disease. Further, there remains an unmet need for alternative and/or improved anti-IL-34 antibodies which have a combination of particularly advantageous properties over prior art anti-IL-34 antibodies, in view of at least one or more properties from the following: 1) desirable association and dissociation rates, 2) potency in neutralization of human IL-34 to achieve an anti-neuroinflammatory response and in vivo efficacy, 3) sufficiently potent as a monotherapy for the treatment and/or prevention of immune-mediated and/or inflammatory disorders; 4) a sustained duration of action; 5) sufficiently limited induction of undesirable cytokine release, 6) acceptably low immunogenicity (i.e., sufficiently non-immunogenic in humans); 7) avoidance of untoward immunocompromise; and/or 8) desirable in vivo stability, physical and chemical stability including, but not limited to, thermal stability, solubility, low self-association, and pharmacokinetic characteristics which are acceptable for development and/or use in the treatment of inflammatory or neuroinflammatory disorders, for example AD.

SUMMARY OF INVENTION

Embodiments of the present invention provide novel anti-human IL-34 and anti-murine IL-34 antibodies. According to some embodiments, the present invention provides antibodies which comprise a light chain variable region (LCVR) and a heavy chain variable region (HCVR), wherein the LCVR comprises complementarity determining regions (CDRs) LCDR1, LCDR2 and LCDR3 and the HCVR comprises CDRs HCDR1, HCDR2 and HCDR3 are selected from the groupings of CDR combinations provided in Table 1. The sequence identifiers used herein are listed in Table 1, and the sequences are provided in the amino acid and nucleotide sequence listing provided herein.

TABLE 1

Amino Acid and Nucleotide Sequences

| | Antibody 1 | Antibody 2 | Antibody 3 |
|---|---|---|---|
| SEQ ID HC | 1 | 13 | 19 |
| SEQ ID LC | 2 | 2 | 20 |
| SEQID HCVR | 3 | 14 | 21 |
| SEQID LCVR | 4 | 4 | 22 |
| SEQID HCDR1 | 5 | 15 | 23 |
| SEQID HCDR2 | 6 | 16 | 24 |
| SEQID HCDR3 | 7 | 17 | 25 |
| SEQID LCDR1 | 8 | 8 | 26 |
| SEQID LCDR2 | 9 | 9 | 27 |
| SEQID LCDR3 | 10 | 10 | 28 |
| SEQ ID: DNA HC | 11 | 18 | 29 |
| SEQ ID DNA LC | 12 | 12 | 30 |

Accordingly, embodiments of the present invention also provide antibodies comprising a LCVR and a HCVR selected from:
  a. the LCVR having the amino acid sequence of SEQ ID NO: 4 and the HCVR having the amino acid sequence of SEQ ID NO: 3;
  b. the LCVR having the amino acid sequence of SEQ ID NO: 4 and the HCVR having the amino acid sequence of SEQ ID NO: 14;
  c. the LCVR having the amino acid sequence of SEQ ID NO: 22 and the HCVR having the amino acid sequence of SEQ ID NO: 21.

According to other embodiments, the present invention also provides antibodies comprising a combination of LCVR and HCVR as described above in a-c, with a hinge region and Fc region selected from SEQ ID NO: 51 and SEQ ID NO: 52.

According to other embodiments, the present invention also provides antibodies comprising a LC and a HC selected from, or having amino acid sequences with at least 95% homology to the amino acid sequences of:
  a. the LC having the amino acid sequence of SEQ ID NO: 2 and the HC having the amino acid sequence of SEQ ID NO: 1;
  b. the LC having the amino acid sequence of SEQ ID NO: 2 and the HC having the amino acid sequence of SEQ ID NO: 13; and
  c. the LC having the amino acid sequence of SEQ ID NO: 20 and the HC having the amino acid sequence of SEQ ID NO: 19.

As used herein "Antibody 1" refers to an antibody having the HCDR1 amino acid sequence of SEQ ID NO: 5, the HCDR2 amino acid sequence of SEQ ID NO: 6, the HCDR3 amino acid sequence of SEQ ID NO: 7, the LCDR1 amino acid sequence of SEQ ID NO: 8, the LCDR2 amino acid sequence of SEQ ID NO: 9, the LCDR3 amino acid sequence of SEQ ID NO: 10, the HCVR amino acid sequence of SEQ ID NO: 3, the LCVR amino acid sequence of SEQ ID NO: 4, the HC amino acid sequence of SEQ ID NO: 1, the LC amino acid sequence of SEQ ID NO: 2, the HC DNA sequence of SEQ ID NO: 11, and the LC DNA sequence of SEQ ID NO: 12. The framework and CDR sequences in each of the antibodies for which sequences are set forth herein are annotated using annotation rules in agreement with the method of North, et al., *J. Mol. Biol.* 2011: 406: 228-256 unless otherwise specified.

As used herein "Antibody 2" refers to an antibody having the HCDR1 amino acid sequence of SEQ ID NO: 15, the HCDR2 amino acid sequence of SEQ ID NO: 16, the HCDR3 amino acid sequence of SEQ ID NO: 17, the LCDR1 amino acid sequence of SEQ ID NO: 8, the LCDR2 amino acid sequence of SEQ ID NO: 9, the LCDR3 amino acid sequence of SEQ ID NO: 10, the HCVR amino acid sequence of SEQ ID NO: 14, the LCVR amino acid sequence of SEQ ID NO: 4, the HC amino acid sequence of SEQ ID NO: 13, the LC amino acid sequence of SEQ ID NO: 2, the HC DNA sequence of SEQ ID NO: 18, and the LC DNA sequence of SEQ ID NO: 12. The framework and CDR sequences in each of the antibodies for which sequences are set forth herein are annotated using annotation rules in agreement with the method of North, et al., *J. Mol. Biol.* 2011: 406: 228-256 unless otherwise specified.

As used herein "Antibody 3" refers to an antibody having the HCDR1 amino acid sequence of SEQ ID NO: 23, the HCDR2 amino acid sequence of SEQ ID NO: 24, the HCDR3 amino acid sequence of SEQ ID NO: 25, the LCDR1 amino acid sequence of SEQ ID NO: 26, the LCDR2 amino acid sequence of SEQ ID NO: 27, the LCDR3 amino acid sequence of SEQ ID NO: 28, the HCVR amino acid sequence of SEQ ID NO: 21, the LCVR amino acid sequence of SEQ ID NO: 22, the HC amino acid sequence of SEQ ID NO: 19, the LC amino acid sequence of SEQ ID NO: 20, the HC DNA sequence of SEQ ID NO: 29, and the LC DNA sequence of SEQ ID NO: 30. The framework and CDR sequences in each of the antibodies for which sequences are set forth herein are annotated using annotation rules in agreement with the method of North, et al., *J. Mol. Biol.* 2011: 406: 228-256 unless otherwise specified.

The carboxy-terminal portion of each HC defines a constant region primarily responsible for effector functions, and in some embodiments of the present invention the antibodies have one or more modifications in the constant region of each HC that reduce effector functions. Preferably, embodiments of the present invention are IgG4 antibodies, and thus contain an IgG4 Fc region, or an Fc region derived from human IgG4, e.g., a modified IgG4 Fc region.

According to some embodiments, modifications in the constant region of both HCs which reduce effector functions, and amino acid substitutions are introduced into the IgG4 hinge and Fc regions. Thus, some embodiments have modifications in the constant region of both HCs which include the amino acid alanine at both residues 230 and 231 (exemplified in HC of Antibody 1, HC of Antibody 2, and SEQ ID NO: 52, respectively), and further modifications in the constant region of both HCs promoting stability, including the amino acid proline at residue 224 (exemplified in HC of Antibody 1, HC of Antibody 2, and for example in SEQ ID NO: 51), and the deletion of the amino acid lysine at residue 443 (exemplified HC of SEQ ID NO.1).

The antibodies of the present invention are believed to have a combination of particularly advantageous properties over prior art anti-IL-34 antibodies, including but not limited to, one or more of the following properties: 1) desirable association and dissociation rates, 2) potency in neutralization of human IL-34 to achieve an anti-neuroinflammatory response and in vivo efficacy, 3) sufficiently potent as a monotherapy for the treatment and/or prevention of immune-mediated and/or inflammatory disorders; 4) a sustained duration of action; 5) sufficiently limited induction of undesirable cytokine release, 6) acceptably low immunogenicity (i.e., sufficiently non-immunogenic in humans); 7) avoidance of untoward immunocompromise; and/or 8) desirable in vivo stability, physical and chemical stability including, but not limited to, thermal stability, solubility, low self-association, and pharmacokinetic characteristics which are acceptable for development and/or use in the treatment of inflammatory or neuroinflammatory disorders, for example AD.

Embodiments of the present invention provide a significant advance over the prior art by providing compositions and methods useful in the prevention, downregulation, or amelioration of inflammatory and/or neuroinflammatory related disorders, through IL-34 neutralization, using a pharmacologically advantageous anti-human IL-34 antibody as provided in the embodiments described herein. Anti-human IL-34 antibodies of the present invention are capable of improving immune and/or inflammatory pathology, or restoring immune homeostasis, preferably, through inhibition of the innate arm of the immune response, and/or abrogation of microgliosis or other monocyte/macrophage lineage cellular activation and or proliferation, thereby directly modifying underlying disease pathology. The use of such antibodies clinically may lead to durable long-term improvement of the disease(s) being treated.

Further, there is a need for diagnostic anti-human IL-34 antibodies that are specific for human IL-34, and possess improved binding affinity, and demonstrate enhanced sensitivity in human IL-34 determinations, and improved enzyme-linked immunosorbent assay (ELISA) assay conditions that result in minimal interference and broad dilutional linearity. According to some aspects of the present invention, anti-human IL-34 antibodies, including human IL-34 neutralizing antibodies, are provided which bind human IL-34 given by SEQ ID NO: 41. Interleukin 34 (IL-34; also known as uncharacterized protein C16orf77) is secreted as a homodimer consisting of 39 kDa monomers. It belongs to no known cytokine family. Human IL-34 is synthesized as a 242 amino acid (AA) precursor that contains a 20 AA signal sequence, and results in a 222 AA mature chain. As used herein IL-34 refers to the mature chain. The mature chain contains one potential site of N-linked glycosylation. Human IL-34 is 71% identical to mouse IL-34 on the amino acid level. IL-34 is expressed in various tissues, including the heart, brain, liver, kidney, spleen, thymus, testes, ovary, small intestine, prostate, and colon, and is most abundant in the spleen. "h IL-34" or "human IL-34" when used herein in reference to an IL-34 polypeptide, unless otherwise stated, refers to wild-type human IL-34, and preferably has the amino acid sequence set forth in SEQ ID NO: 41, which is mature IL-34 having the leader sequence removed. (See, for example, Lin et. al., Science (2008) Vol. 320, Issue 5877, pp. 807-811).

An exemplary human IL-34 (including the 20 AA signal peptide sequence which is removed to yield the mature polypeptide) is:

MPRGFTWLRYLGIFLGVALGNEPLEMWPLTQNEECTVTGFLRDKLQYRS

RLQYMKHYFPINYKISVPYEGVFRIANVTRLQRAQVSERELRYLWVLVS

LSATESVQDVLLEGHPSWKYLQEVETLLLNVQQGLTDVEVSPKVESVLS

LLNAPGPNLKLVRPKALLDNCFRVMELLYCSCCKQSSVLNWQDCEVPSP

QSCSPEPSLQYAATQLYPPPPWSPSSPPHSTGSVRPVRAQGEGLLP (SEQ ID NO: 41, see NCBI Ref Seq. No. NP_

689669.2, Mar. 1, 2018).

According to some aspects of the present invention, anti-murine IL-34 antibodies, including murine IL-34 neutralizing antibodies, are provided which bind human IL-34 given by SEQ ID NO. 42. An exemplary murine IL-34 (including the 20 AA signal peptide sequence which is removed to yield the mature polypeptide) is:

MPWGLAWLYCLGILLDVALGNENLEIWTLTQDKECDLTGYLRGKLQYK

NRLQYMKHYFPINYRIAVPYEGVLRVANITRLQKAHVSERELRYLWVLV

SLNATESVMDVLLEGHPSWKYLQEVQTLLENVQRSLMDVEIGPHVEAVL

SLLSTPGLSLKLVRPKALLDNCFRVMELLYCSCCKQSPILKWQDCELPR

LHPHSPGSLMQCTATNVYPLSRQTPTSLPGSPSSSHGSLP (SEQ ID

NO: 42, see NCBI Ref Seq. No. NP_001128572.1,

Mar. 1, 2018).

As used herein, "human anti-IL34 antibody" or "anti-human IL-34 antibody" refers to an antibody that binds to human IL-34, and when administered in vitro or in vivo, results in an IL-34 activity-neutralizing and/or blocking response, such as at least one significantly lessened desired activity, for example a desired reduction in IL-34 signaling as evidenced by a change in an IL-34 responsive molecular or cellular endpoint. For instance, microglia number, density, or phenotype in the CNS, is an example of an IL-34 responsive molecular or cellular effect. As used herein, the terms "signaling" and "signal transduction" and "IL-34-mediated", as they relate to IL-34, refer to cellular and/or intercellular responses which result from the activity of IL-34.

The term "antibody," as used herein, refers to an immunoglobulin molecule that binds an antigen. Embodiments of an antibody include a monoclonal antibody, polyclonal antibody, human antibody, humanized antibody, chimeric antibody or conjugated antibody. The antibodies can be of any class (e.g., IgG, IgE, IgM, IgD, IgA) and any subclass (e.g., IgG1, IgG2, IgG3, IgG4). An exemplary antibody is an immunoglobulin G (IgG) type antibody comprised of four polypeptide chains: two heavy chains (HC) and two light chains (LC) that are cross-linked via inter-chain disulfide bonds. LCs are classified as kappa or lambda, which are each characterized by a specific constant region. Embodiments of the present invention may comprise an IgG1 or IgG4 antibody, and further comprise kappa light chains or lambda light chains. Preferably antibodies of the present invention comprise light chain constant regions which are kappa constant regions.

HCs are classified as gamma, mu, alpha, delta, or epsilon, and define the isotype of an antibody as IgG, IgM, IgA, IgD, or IgE, respectively. The amino-terminal portion of each of the four polypeptide chains includes a variable region of about 100-125 or more amino acids primarily responsible for antigen recognition. The carboxyl-terminal portion of each of the four polypeptide chains contains a constant region primarily responsible for effector functions. Each heavy chain is comprised of a heavy chain variable region (VH) and a heavy chain constant region. The constant region of the heavy chains contains CH1, CH2, and CH3 domains. CH1 comes after the HCVR; the CH1 and HCVR form the heavy chain portion of an antigen-binding (Fab) fragment, which is the part of an antibody that binds antigen(s). CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab.

The antibodies of the present invention include IgG HCs which can be further divided into subclasses, e.g., IgG1, IgG2, IgG3, IgG4, and embodiments of the present invention may include one or more modifications in the constant region of each HC, for example that enhance or reduce effector function. The term "Fc region" as used herein refers to a region of an antibody, which comprises the CH2 and CH3 domains of the antibody heavy chain. Optionally, the Fc region may include a portion of the hinge region or the entire hinge region of the antibody heavy chain. IgG1 is known to induce antibody-dependent cell cytotoxicity (ADCC) and complement-dependent cytotoxicity (CDC), and Fc mutations described herein may reduce aggregation, reduce or enhance ADCC or CDC activities, (or other functions), and/or modify the pharmacokinetics of the antibodies. Embodiments of anti-human IL-34 antibodies described herein have reduced binding to the FcγR and C1q receptors, thereby reducing or eliminating the cytotoxicity which may be induced by antibodies with wild type IgG Fc regions. Thus, according to some embodiments, mutations are introduced in the Fc region at positions as described herein. Patient safety can be improved with sufficiently reduced or eliminated effector functions of such anti-human IL-34 antibodies comprising a modified Fc region, and in combination with other properties described herein, provide therapeutic agents with an improved profile of useful activities while avoiding undesirable activities.

When expressed in certain biological systems, antibodies are glycosylated in the Fc region. Typically, glycosylation occurs in the Fc region of the antibody at a highly conserved N-glycosylation site. N-glycans typically attach to asparagine. Antibodies may be glycosylated at other positions as well. Antibodies of the present invention are monoclonal antibodies. Monoclonal antibodies are antibodies derived from a single copy or clone including, for example, any eukaryotic, prokaryotic or phage clone, and not defined by the method by which it is produced. Monoclonal antibodies can be produced, for example, by hybridoma technologies, recombinant technologies, phage display technologies, synthetic technologies, e.g., CDR-grafting, or combinations of such or other technologies known in the art. The present invention contemplates the antibodies of the present invention are human or humanized antibodies. In the context of monoclonal antibodies, the terms "human" and "humanized" are well-known to those of ordinary skill in the art (Weiner L J, J. Immunother. 2006; 29: 1-9; Mallbris L, et al., J. Clin. Aesthet. Dermatol. 2016; 9: 13-15). Exemplary embodiments of antibodies of the present invention also include antibody fragments or antigen-binding fragments, which comprise at least a portion of an antibody retaining the ability to specifically interact with an antigen such as Fab, Fab', F(ab')2, Fv fragments, scFv antibody fragments, disulfide-linked Fvs (sdFv), a Fd fragment and linear antibodies.

The amino terminal portion of each LC and HC includes a variable region of about 100-120 amino acids primarily responsible for antigen recognition via the CDRs contained therein. The VH and VL regions can be further subdivided into regions of hyper-variability, termed complementarity determining regions (CDRs), interspersed with regions that are more conserved, termed framework regions (FR). The CDRs are exposed on the surface of the protein and are important regions of the antibody for antigen binding specificity. Each VH and VL is composed of three CDRs and four FRs, arranged from amino-terminus to carboxyl-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues that form specific interactions with the antigen. The functional ability of an antibody to bind a specific antigen is largely influenced by the six CDRs. Assignment of amino acid residues to the CDRs may be done according to the well-known schemes, including those described in Kabat (Kabat et al., "Sequences of Proteins of Immunological Interest," National Institutes of Health, Bethesda, Md. (1991)), Chothia (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)), North (North et al., "A New Clustering of Antibody CDR Loop Conformations", Journal of Molecular Biology, 406, 228-256 (2011)), or IMGT (the international ImMunoGeneTics database available on at www.imgt.org; see Lefranc et al., Nucleic Acids Res. 1999; 27:209-212).

For the purposes of the present invention, and except where specified otherwise, the North CDR definitions are used for the anti-IL-34 antibodies described herein, and assignment of amino acids to CDR domains within the LCVR and HCVR regions. Below is table of CDR sequences for Antibody 1 based on North definitions. The skilled artisan can also apply alternative definitions of Kabat, Chothia, and/or IMGT, to specify CDR's according to those conventions for Antibodies of the present invention including Antibodies 1-3 in Table 1.

| Exemplary CDRs of Antibody 1 (or Antibodies of the present disclosure) | | | | | | |
|---|---|---|---|---|---|---|
| Ab | HCDR1 | HCDR2 | HCDR3 | LCDR1 | LCDR2 | LCDR3 |
| North | AASGFTFSSY ATS (SEQ ID NO: 5) | AISHSGRSTY YADSVKG (SEQ ID NO: 6) | ARGRSSLDT (SEQ ID NO: 7) | RASQSISS AYLA (SEQ ID NO: 8) | YASSIRPT (SEQ ID NO: 9) | SQYGDSLS (SEQ ID NO: 10) |

Antibody embodiments of the present invention possess a combination of several pharmacologically useful and important activities, and in one respect are capable of binding with high affinity to human IL-34 and high specificity for human IL-34, as well as other useful properties. The terms "bind" and "binds" as used herein are intended to mean, unless indicated otherwise, the ability of a protein or molecule to form attractive interactions with another protein or molecule, which results in proximity of the two proteins or molecules as determined by common methods known in the art. The phrase "specifically binds", as used herein in reference to the affinity of an anti-IL-34 antibody for human IL-34, is intended to mean, unless indicated otherwise, a $K_D$ of preferably less than about $1 \times 10^{-11}$ M, even more preferably, between about $1 \times 10^{-11}$ M and about $1 \times 10^{-12}$ M, as determined by common methods known in the art, including by use of a SPR biosensor, and/or MSD, essentially as described herein. The phrase "specifically binds" also indicates the relative affinity of an anti-IL-34 antibody for human IL-34, as compared to other antigens, wherein the affinity for human IL-34 results in a specific recognition of human IL-34.

Antibody embodiments of the present invention may be expressed and produced by a variety of techniques known in the art from constructs comprising sequences of the present embodiments. The terms "nucleic acid" or "polynucleotide", as used interchangeably herein, refer to polymers of nucleotides, including single-stranded and/or double-stranded nucleotide-containing molecules, such as DNA, cDNA and RNA molecules, incorporating native, modified, and/or analogs of, nucleotides. Polynucleotides of the present disclosure may also include substrates incorporated therein, for example, by DNA or RNA polymerase or a synthetic reaction. A DNA molecule of the present invention is a DNA molecule that comprises a non-naturally occurring polynucleotide sequence encoding a polypeptide having the amino acid sequence of at least one of the polypeptides in an antibody of the present invention (e.g., heavy chain, light chain, variable heavy chain, and variable light chain).

An isolated DNA encoding a HCVR or LCVR region can be converted to a full-length heavy chain gene by operably linking the respective HCVR or LCVR-encoding DNA to another DNA molecule encoding heavy or light chain constant regions, to form a heavy or light chain respectively. The sequences of human, as well as other mammalian, heavy chain constant region genes are known in the art. DNA fragments encompassing these regions can be obtained, e.g., by standard PCR amplification.

The polynucleotides of the present invention can be expressed in a host cell after the sequences have been operably linked to an expression control sequence. The expression vectors are typically replicable in the host organisms either as episomes, or as an integral part of the host chromosomal DNA. Commonly, expression vectors will contain selection markers, e.g., tetracycline, neomycin, and dihydrofolate reductase, to permit detection of those cells transformed with the desired DNA sequences. The vectors containing the polynucleotide sequences of interest (e.g., the polynucleotides encoding the polypeptides of the antibody and expression control sequences) can be transferred into the host cell by well-known methods, which vary depending on the type of cellular host.

The antibodies of the present invention can readily be produced in mammalian cells, non-limiting examples of which includes CHO, NS0, HEK293 or COS cells. The host cells are cultured using techniques well known in the art. Mammalian expression of antibodies typically results in glycosylation. Glycosylation of antibodies is typically either N-linked or O-linked. N-linked glycosylation refers to the attachment of a carbohydrate moiety to the side chain of an asparagine residue. O-linked glycosylation refers to the attachment of a sugar, for example N-acetylgalactosamine, galactose, or xylose to a hydroxyamino acid. Typically, glycosylation occurs in the Fc region of the antibody at a highly conserved N-glycosylation site (e.g., position 297 in IgG1, according to IMGT or EU Index numbering). Glycosylation sites can be modified to alter glycosylation (e.g., blocking or reducing glycosylation or altering the amino acid sequence to produce additional or diverse glycosylation).

Mammalian expression of antibodies from IgG subclasses can result in clipping of C-terminal amino acids from one or both heavy chains; for example, one or two C-terminal amino acids can be removed for IgG1 antibodies. For IgG1 antibodies, if a C-terminal lysine is present, then it may be truncated or clipped off from the heavy chain during expression. Additionally, a penultimate glycine may also be truncated or clipped off from the heavy chain as well.

Mammalian expression of antibodies can also result in the modification of N-terminal amino acids. For example, where the N-terminal most amino acid of a heavy chain or light chain is a glutamine, it may be modified into pyro-glutamic acid.

An antibody of the present invention, or a pharmaceutical composition comprising the same, may be administered by parenteral routes, non-limiting examples of which are subcutaneous administration and intravenous administration. An antibody of the present invention may be administered to a patient with pharmaceutically acceptable carriers, diluents, or excipients in single or multiple doses. Pharmaceutical compositions of the present invention can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

Uses of Antibody Embodiments of the Present Invention:

According to some embodiments, the anti-IL-34 antibodies of the present invention are useful in the treatment of immune-mediated diseases. As used herein, the term "immune-mediated disease" or "inflammatory disease or disorder" are used interchangeably and refer to undesirable conditions that arise from an inappropriate, or excessive immune responses in which IL-34 inhibition results in more homeostatic and less pathological responses. The term "immune-mediated disease" or "inflammatory disorder" is meant to include such conditions, whether they be mediated by microglia or macrophage cellular immune responses, or those of similar tissue-resident cell types, such as histiocytes, Kupffer cells, alveolar macrophages, intestinal macrophages, macrophage-like synoviocytes, or Langerhans cells. Exemplary diseases contemplated to be treated by the antibodies of the invention described herein include Alzheimer's Disease; a Tauopathy disease; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

In some more specific embodiments, the immune-mediated disease is Alzheimer's Disease (AD). According to other embodiments of the present invention, the anti-IL-34 antibodies are useful in diagnostic applications for immune-mediated diseases. In some embodiments, the immune-mediated diseases are at least one of AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

The present invention further provides pharmaceutical compositions comprising an anti-IL-34 antibody of the present invention and one or more pharmaceutically acceptable carriers, diluents or excipients. Further, the present invention provides a method of treating an immune-mediated disease, such as AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD), comprising administering to a patient in need thereof a pharmaceutical composition of the present invention.

In addition, the present invention provides a method of treating immune-mediated diseases. More particularly, the present invention provides a method of treating immune-mediated diseases, including AD; Sjogren's syndrome (SS);

Rheumatoid arthritis (RA); inflammatory bowel disease (IBD), atopic dermatitis, kidney disease, sepsis, and/or non-alcoholic fatty liver disease (NAFLD), comprising administering to a patient in need thereof an effective amount of an anti-IL-34 antibody of the present invention.

The present invention also provides an anti-IL-34 antibody of the present invention for use in therapy. More particularly, the present invention provides an anti-IL-34 antibody of the present invention for use in treatment of immune-mediated diseases including AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

In certain embodiments, the present invention provides the use of an anti-IL-34 antibody of the present invention in the manufacture of a medicament for the treatment of one or more immune-mediated diseases including AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

Antibodies of the present invention are useful in the identification of immune-mediated disorders wherein IL-34 may contribute to the etiopathogenesis of the disorder. In further embodiments, the present invention provides a method of treating an immune-mediated disease in a patient. Such methods comprise the steps of contacting a patient sample with an anti-IL-34 antibody and detecting binding between human IL-34 in the patient sample and the antibody; and diagnosing the patient as having; at risk for; in need of treatment for; and/or at risk of symptoms relating to an immune-mediated disease when the presence of IL-34 in the patient sample is detected as above a reference value observed in non-diseased individuals (See for example Xie, H. H., et al. *Elevated Serum Interleukin-34 Level in Patients with Systemic Lupus Erythematosus Is Associated with Disease Activity*. Sci Rep 8, 3462 (2018). According to some more specific embodiments of the methods of treating provided herein, such methods further include the steps of determining the reference value including the further steps of contacting a control standard with a first antibody which binds the same first epitope region of IL-34 as used in contacting the patient sample; contacting the control standard with a second antibody having a detectable label and which binds the same second epitope region of IL-34 as used in contacting the patient sample; and detecting a signal provided by the detectable signal. In some specific embodiments, the anti-IL-34 antibody comprises a combination of LC and HC CDRs provided in Table 1. In further embodiments, the second antibody comprises a combination of LCVR and HCVR provided in Table 1. According to some embodiments, the reference value is approximately 10-30 pg/mL, for example from CNS tissue lysates. In certain embodiments, the immune-mediated disease is one of AD; Sjogren's syndrome (SS); Rheumatoid arthritis (RA); inflammatory bowel disease (IBD), atopic dermatitis, kidney disease, sepsis, and/or non-alcoholic fatty liver disease (NAFLD). In some embodiments, the patient sample is one of CSF, blood, serum, a tissue lysate, or plasma. According to some embodiments, the method further includes the steps of contacting the patient sample with a second anti-IL-34 antibody which binds a second epitope region of IL-34, and has a detectable label, and detecting a signal provided by the detectable signal. In further embodiments, the second antibody comprises a combination of LC and HC CDRs provided in Table 1. In further embodiments, the second antibody comprises a combination of LCVR and HCVR provided in Table 1. According to certain embodiments, the first and second anti-IL-34 antibodies do not bin together.

According to some embodiments, the present invention provides a method of detecting IL-34 in a patient sample comprising the steps of contacting the patient sample with a first antibody which binds a first epitope region of IL-34; contacting the patient sample with a second antibody which binds a second epitope region of IL-34 and has a detectable label; and detecting a signal provided by said detectable label. In some embodiments, the patient sample is one of blood, serum, a tissue lysate or plasma. According to some more specific embodiments, the first epitope region of IL-34 partially overlaps with the second epitope region of IL-34. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1.

According to some embodiments of the present invention, a method of quantifying IL-34 in a patient sample is provided. Such method includes the steps of contacting the patient sample with a first antibody which binds a first epitope region of IL-34; contacting the patient sample with a second antibody which binds a second epitope region of IL-34 and said has a detectable label; and detecting the signal provided by said detectable label; contacting a control standard with a first antibody which binds the same first epitope region of IL-34 (as used in contacting the patient sample); contacting the control standard with a second antibody which binds the same second epitope region of IL-34 (as used in contacting the patient sample) and having a detectable label; and detecting a signal provided by said detectable signal. In some embodiments, the patient sample is one of blood, serum or plasma, or a tissue lysate. According to some more specific embodiments, the first epitope region of IL-34 partially overlaps with the second epitope region of IL-34. Further, in some embodiments, said steps of contacting with the first and second antibodies occurs simultaneously. In some specific embodiments, the first antibody comprises a combination of LC and HC CDRs provided in Table 1. In further embodiments, the first antibody comprises a combination of LCVR and HCVR provided in Table 1. In some specific embodiments, the second antibody comprises a combination of LC and HC CDRs provided in Table 1. In further embodiments, the second antibody comprises a combination of LCVR and HCVR provided in Table 1.

According to some embodiments, a method of diagnosing an immune-mediated disease is provided. Such method comprises the steps of contacting a patient sample with an anti-IL-34 antibody and detecting binding between IL-34 in the patient sample and the antibody. According to some specific embodiments, the method of diagnosing includes diagnosing the patient as having; at risk for; in need of treatment for; and/or at risk of symptoms relating to an immune-mediated disease when the presence of IL-34 in the patient sample is detected as above a reference value. According to some more specific embodiments, such methods further include the steps of determining the reference value including the steps of contacting a control standard with a first antibody which binds the same first epitope region of IL-34 as used in contacting the patient sample; contacting the control standard with a second antibody having a detectable label and which binds the same second epitope region of IL-34 as used in contacting the patient sample; and detecting a signal provided by the detectable signal. In some embodiments, the first antibody comprises a combination of LC and HC CDRs provided in Tables 1. Some embodiments of the method of diagnosing an immune-mediated disease, provided herein, further includes the steps of contacting the patient sample with a second anti-IL-34 antibody which binds a second epitope region of IL-34 and has a detectable label; and detecting a signal provided by the detectable label. In some specific embodiments, the anti-IL-34 antibody comprises a combination of LC and HC CDRs provided in Table 1. In further embodiments, the antibody comprises a combination of LCVR and HCVR provided in Table 1. According to specific embodiments, the first epitope region of IL-34 partially overlaps with the second epitope region of IL-34. According to certain embodiments, the first and second antibodies do not bin together. According to further embodiments, the reference value is approximately a range from 10-30 pg/mL from CNS tissue lysates, and/or as determined by the skilled artisan for the appropriate reference group and sample source. In further embodiments, the immune-mediated disease is one of AD; a tauopathy; Sjogren's syndrome (SS); Rheumatoid arthritis (RA); inflammatory bowel disease (IBD), atopic dermatitis, kidney disease, sepsis, and/or non-alcoholic fatty liver disease (NAFLD).

In an embodiment the present invention provides a method of determining the human IL-34 level in a bodily fluid comprising: (a) contacting the bodily fluid with an anti-human IL-34 diagnostic monoclonal antibody, or antigen-binding fragment thereof, that specifically binds to human IL-34 consisting of the amino acid sequence as in SEQ ID NO: 41, the antibody, or antigen-binding fragment thereof, comprising: light chain complementarity determining regions LCDR1, LCDR2, and LCDR3 comprising the amino acid sequences (SEQ ID NO: 8), (SEQ ID NO: 9), and (SEQ ID NO: 10), respectively, and heavy chain complementarity determining regions HCDR1, HCDR2, and HCDR3 comprising the amino acid sequences (SEQ ID NO: 15), (SEQ ID NO: 16), and (SEQ ID NO: 17), respectively; (b) optionally, removing any non-specifically bound monoclonal antibody or, antigen-binding fragment thereof; and (c) detecting and/or quantifying the amount of monoclonal antibody, or antigen-binding fragment thereof, which is specifically bound to human IL-34. Preferably, wherein said bodily fluid is blood, serum or plasma, or cerebrospinal fluid, and said contacting occurs ex vivo.

Tauopathy diseases include but are not limited to, Alzheimer's disease (AD), Pick's disease (PiD), progressive supranuclear palsy (PSP), corticobasal degeneration (CBD), argyrophilic grain disease, Down's Syndrome, chronic traumatic encephalopathy (CTE), traumatic brain injury (TBI), frontotemporal dementia with Parkinsonism linked to chromosome 17 (FTDP-17), Parkinsonism-dementia complex of Guam, Niemann-Pick disease type C, myotonic dystrophy (See Li, C., Gotz, J. *Tau*-based therapies in neurodegeneration: opportunities and challenges. Nat Rev Drug Discov 16, 863-883 (2017)).

In embodiments of the invention a patient is a human who has been diagnosed as having a medical risk, condition or disorder, such as one of the diseases or disorders described herein, in need of treatment with an antibody described herein. In those instances where the disorders which can be treated by the methods of the present invention are known by established and accepted classifications, such as Alzheimer's Disease; a tauopathy disease; Sjogren's syndrome (SS); Rheumatoid arthritis (RA); inflammatory bowel disease (IBD), atopic dermatitis, kidney disease, sepsis, and/or non-alcoholic fatty liver disease (NAFLD), their classifications can be found in various well-known medical texts. For example, at present, the 5th edition of the Diagnostic and Statistical Manual of Mental Disorders (DSM-5), provides a diagnostic tool for identifying certain disorders described herein. Also, the International Classification of Diseases, Tenth Revision (ICD-10), provides classifications for certain disorders described herein. The skilled artisan will recognize that there are alternative nomenclatures, nosologies, and classification systems for diseases and disorders described herein, including those as described in the DSM-5 and ICD-10, and that terminology and classification systems evolve with medical scientific progress.

The term "treating" (or "treat" or "treatment") refers to slowing, interrupting, arresting, alleviating, stopping, reducing, or reversing the progression or severity of an existing symptom, disorder, condition, or disease.

As used herein, the term "innate immunity" includes the arm of the immune response which, in contrast to the adaptive arm of the immune response, is required to initiate and maintain an adaptive immune response (antibody and T cell responses).

"Effective amount" means the amount of an anti-human IL-34 antibody of the present invention, or a pharmaceutical composition comprising such an antibody, that will elicit the biological or medical response of or desired therapeutic effect on a tissue, system, or human, that is being sought by the treating health professional. As used herein, the term "effective response" of a patient or a patient's responsiveness to treatment refers to the clinical or therapeutic benefit imparted to a patient upon administration an antibody of the present disclosure. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. Such benefit includes any one or more of: a decreased level of inflammation or immune activation, stabilized immune-mediated disease or disorder; or improving signs or symptoms of an immune-mediated disorder. Alternatively, such benefit includes any one or more of the following: an increased immune tolerance of transplanted organs; stabilized autoimmune disease or disorder; or improving signs or symptoms of an autoimmune disorder.

A potential advantage of methods disclosed herein is the possibility of producing marked and/or prolonged relief in a patient suffering from an immune-mediated disorder, or neuroinflammatory disorder, with an acceptable safety profile including acceptable tolerability, toxicities and/or adverse events, so that the patient benefits from the treatment method overall. The efficacy of the treatment of the present disclosure can be measured by various endpoints that are commonly used in evaluating treatments for various immune-mediated disorders. Other approaches to determining efficacy of any particular therapy of the present invention can be optionally employed, including, for example, immune cell activation markers, measures of inflammation, cell-cycle dependent biomarker measurement and visualization, and/or measurement of response through various inflammation or immune or tissue specific biomarker assessments.

An effective amount can be readily determined by one skilled in the art, using known techniques, and by observing results obtained under analogous circumstances. An effective amount of an anti-human IL-34 antibody of the present invention may be administered in a single dose or in multiple doses. Furthermore, an effective amount of an antibody of the invention may be administered in multiple doses of amounts that would be less than an effective amount if not administered more than once. In determining the effective amount for a patient, a number of factors are considered by the attending medical practitioner, including, but not limited to: the patient's size (e.g., weight or mass), body surface area, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances known to medical practitioners.

A weekly, every two week, monthly, or quarterly parenteral (including, but not limited to, subcutaneous, intramuscular, and/or intravenous) dose can be from about 0.5 mg/kg to about 50 mg/kg.

A weekly, every two week, monthly, or quarterly parenteral (including, but not limited to, subcutaneous, intramuscular, and/or intravenous) dose can be from about 0.5 mg/kg to about 10 mg/kg, from about 1 mg/kg to about 10 mg/kg, from about 2 mg/kg to about 10 mg/kg, from about 3 mg/kg to about 10 mg/kg, from about 4 mg/kg to about 10 mg/kg, from about 5 mg/kg to about 10 mg/kg, from about 6 mg/kg to about 10 mg/kg, from about 7 mg/kg to about 10 mg/kg from about 8 mg/kg to about 10 mg/kg, from about 1 mg/kg to about 8 mg/kg, from about 2 mg/kg to about 8 mg/kg, from about 3 mg/kg to about 8 mg/kg, from about 4 mg/kg to about 8 mg/kg, from about 5 mg/kg to about 8 mg/kg, from about 6 mg/kg to about 8 mg/kg, from about 1 mg/kg to about 6 mg/kg, from about 2 mg/kg to about 6 mg/kg, from about 3 mg/kg to about 6 mg/kg, from about 4 mg/kg to about 6 mg/kg, from about 5 mg/kg to about 6 mg/kg, from about 1 mg/kg to about 5 mg/kg, from about 2 mg/kg to about 5 mg/kg, from about 3 mg/kg to about 5 mg/kg, from about 4 mg/kg to about 5 mg/kg, from about 1 mg/kg to about 4 mg/kg, from about 2 mg/kg to about 4 mg/kg, from about 3 mg/kg to about 4 mg/kg, from about 3.5 mg/kg to about 5 mg/kg, or about 4 mg/kg to about 5 mg/kg.

A weekly, every two weeks, monthly, or quarterly parenteral (including, but not limited to, subcutaneous, intramuscular, and/or intravenous) dose can be, for example, from about 50 mg to about 500 mg, from about 75 mg to about 500 mg, from about 100 mg to about 500 mg, from about 125 mg to about 500 mg, from about 250 mg to about 500 mg, from about 300 mg to about 500 mg, from about 350 mg to about 500 mg, from about 400 mg to about 500 mg, from about 450 mg to about 500 mg, from about 50 mg to about 400 mg, from about 75 mg to about 400 mg, from about 100 mg to about 400 mg, from about 125 mg to about 400 mg, from about 250 mg to about 400 mg, from about 300 mg to about 400 mg, from about 350 mg to about 400 mg, from about 50 mg to about 300 mg, from about 75 mg to about 300 mg, from about 100 mg to about 300 mg, from about 125 mg to about 300 mg, from about 150 mg to about 300 mg, from about 175 mg to about 300 mg, from about 200 mg to about 300 mg, from about 250 mg to about 300 mg, from about 50 mg to about 250 mg, from about 75 mg to about 250 mg, from about 100 mg to about 250 mg, from about 125 mg to about 250 mg, from about 150 mg to about 250 mg, from about 175 mg to about 250 mg, from about 200 mg to about 250 mg, from about 75 mg to about 250 mg, from about 50 mg to about 200 mg, from about 75 mg to about 200 mg, from about 100 mg to about 200 mg, from about 125 mg to about 200 mg, from about 150 mg to about 200 mg, from about 175 mg to about 200 mg, from about 50 mg to about 175 mg, from about 75 mg to about 175 mg, from about 100 mg to about 175 mg, from about 125 mg to about 175 mg, or from about 150 mg to about 175 mg.

However, doses below or above the doses mentioned herein are also envisioned, especially considering dosage considerations known to those skilled in the art and/or described herein. Progress of the patient being treated may be monitored by periodic assessment, and the dose adjusted accordingly if necessary.

A potential advantage of methods disclosed herein is the possibility of producing marked and/or prolonged relief in a patient suffering from an immune-mediated disorder, or neuroinflammatory disorder, with an acceptable safety profile including acceptable tolerability, toxicities and/or adverse events, so that the patient benefits from the treatment method overall, and more particularly the antibodies of the present invention will provide effective treatment while avoiding clinically undesirable immunosuppression and/or immune associated adverse events such as "cytokine storm" or significant cytokine release. Antibodies of the present invention may be useful for the treatment of cytokine storm, or otherwise adverse cytokine release. As used herein, "significant cytokine release" refers to a significant increase in measurable cytokines that can be detected by methods known to persons of ordinary skill. For example, significant cytokine release may be detected in human blood samples by ELISA, wherein cytokine levels from unstimulated blood are compared to cytokine levels with blood incubated with antibody. In some such studies, for example, a significant cytokine release may be detected if the levels of IL-6, or IL-8, or IFN-γ are at least three-fold higher in blood incubated with antibody compared to levels in unstimulated blood. Preferably, treatment of an immune-mediated disorder as described in the embodiments herein will occur wherein the patient will not experience significant cytokine release.

EXAMPLES

Figure 1:
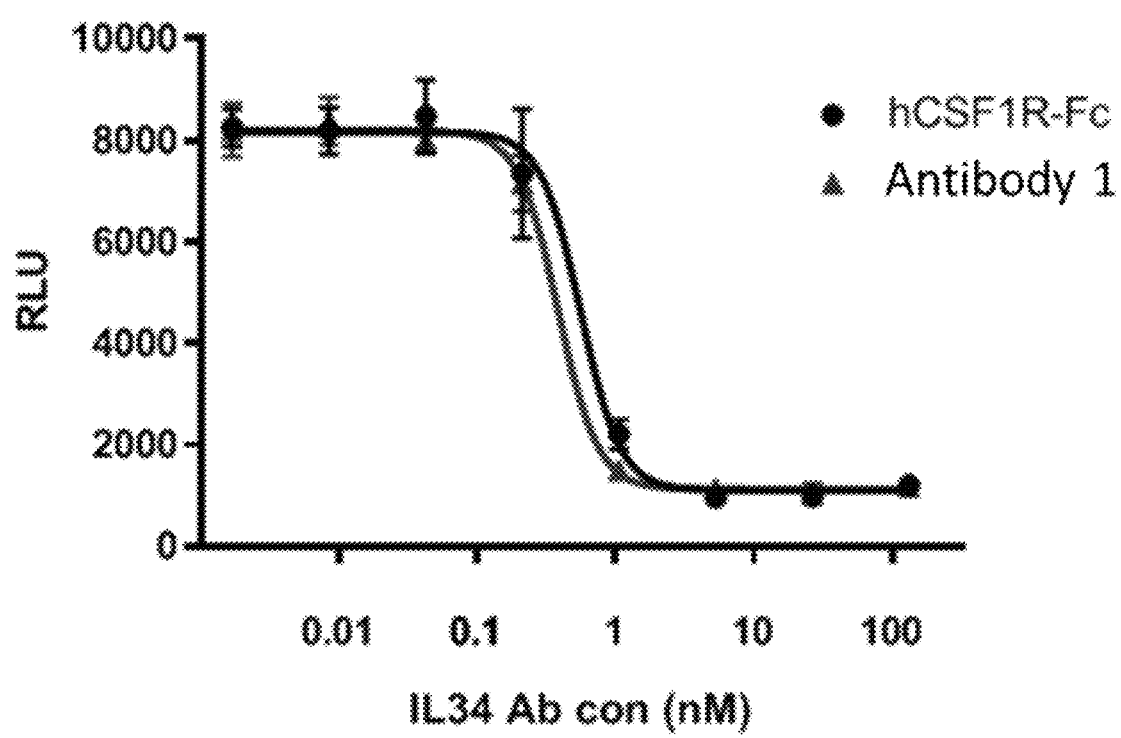
FIG. 1 shows Antibody 1 neutralization of human IL-34 induced luciferase reporter activity in hCSF1R expressing 293 SRE cells.

The following examples are offered to illustrate, but not to limit, the claimed invention. The results of the following assays demonstrate that the exemplified monoclonal antibodies, and/or antigen-binding fragments thereof of the present invention bind and/or neutralize IL-34, and therefore may be used for treating immune-mediated and inflammatory diseases described herein.

Example 1: Antibody Generation, Expression and Purification

A panel of human anti-IL-34 antibodies is obtained using human antibody phage display libraries and screened to identify reagents that could be effective IL-34 neutralizing antibodies. Mutations are systematically introduced into individual complementarity determining regions (CDRs) of each antibody and the resulting libraries are subjected to multiple rounds of selection with decreasing concentrations of antigen and/or increasing periods of dissociation, in order to isolate clones with improved affinities. The sequences of individual variants are determined and used to construct a combinatorial library which is subjected to an additional round of selection with increased stringency to identify additive or synergistic mutational pairings between the individual CDR regions. Individual combinatorial clones are sequenced, and binding characteristics are determined. In order to further increase the affinity to IL-34, these combinatorial clones are subjected to additional rounds of single and combinatorial mutagenesis. This screening can be conducted against human or mouse IL-34 to increase affinity against a selected species (for example Antibody 1 for human IL-34, and Antibody 3 for mouse IL-34). Selected antibodies can also be mutagenized to fix post-translational modifications such as methionine oxidation, while retaining binding affinity to IL-34. Additionally, framework (FW) substitutions can be made to the antibody to revert these FW1 sequences to their germline state in order to reduce potential immunogenicity risk.

Engineered and/or optimized anti-IL-34 antibodies referred to herein as Antibody 1, Antibody 2, and/or Antibody 3 are obtained, having the amino acid sequences of the variable regions of the heavy chain and light chain, and the complete heavy chain and light chain amino acid sequences, and the nucleotide sequences encoding the same, as listed below in the section entitled "Listing of Amino Acid and Nucleotide Sequences". The SEQ ID NO's corresponding to these fragments are shown below in Table 1, as well as the light chain and heavy chain CDR amino acid sequences.

The exemplified anti-IL-34 antibodies of the present invention can be expressed and purified essentially as follows. An appropriate host cell, such as HEK 293, NS0 or CHO, can be either transiently or stably transfected with an expression system for secreting antibodies using an optimal predetermined HC:LC vector ratio (such as 1:3 or 1:2) or a single vector system encoding both the HC and the LC. Clarified media, into which the antibody has been secreted, is purified using any of many commonly-used techniques. For example, the medium may be applied to a Protein A or G column, for instance a Mab Select® column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer, pH 7.0 to 10 mM sodium citrate buffer, pH 3.0, or phosphate buffered saline pH 7.4 to 100 mM glycine buffer, pH 3.0). Antibody fractions may be detected, such as by SDS-PAGE, and then may be pooled. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, or ion exchange, multimodal, or hydroxyapatite chromatography. The purity of the antibody after these chromatography steps is greater than 99%. The product may be immediately frozen at −70° C., or may be lyophilized, or preserved in 4° C. for immediate use. Amino acid SEQ ID NOs for exemplified human antibodies of the present invention are shown below in Table 1.

The expression plasmid contains cDNA versions of the LC and HC genes for Antibody 1 (for example, a DNA sequence of SEQ ID NO:12 encoding a HC of exemplified Antibody 1 presented in Table 1, and a DNA sequence encoding a LC amino acid sequence according to Table 1, for example, a DNA sequence of SEQ ID NO:13 encoding a LC of exemplified Antibody 1 presented in Table 1); and are expressed from a commonly-used and suitable construct for this purpose, such as one based on human cytomegalovirus major immediate early promoters. The LC and HC genes are flanked by inverted terminal repeat (ITR) sequences recognized by a transposase enzyme. The parent cell line is co-transfected with the expression plasmid and a transposase mRNA which enables transient expression of the transposase enzyme, to promote stable integration of the Antibody 1 gene expression cassette into the genomic DNA.

The selected bulk culture is subjected to single-cell cloning using Fluorescence-Activated Cell Sorting (FACS) technology. The clonally-derived cell lines are expanded and screened for Antibody 1 production. A clonally-derived cell line is selected and established. This cell line is generated without any animal component-containing materials and used for production.

Clarified medium, into which the antibody is secreted, is applied to a Protein A affinity column that is equilibrated with a compatible buffer, such as phosphate buffered saline (pH 7.4) or 20 mM Tris with 150 mM sodium chloride (pH 8.0). The column is washed with 1M NaCl to remove nonspecific binding components. Bound antibody is eluted, for example, with sodium citrate at pH (approx.) 3.5 and fractions are neutralized with 1M Tris buffer. Antibody fractions are detected, such as by SDS-PAGE or analytical size-exclusion, and then pooled. Soluble aggregate and multimers may be effectively removed by common techniques, including size exclusion, hydrophobic interaction, ion exchange, or hydroxyapatite chromatography. An exemplified anti-IL-34 antibody of the present invention is concentrated and/or sterile filtered using common techniques. The purity of an exemplified antibody after these chromatography steps is greater than 95%. An exemplified anti-IL-34 antibody of the present invention may be immediately frozen at −70° C. or stored at 4° C. for several months.

Example 2: Characterization of the Anti-IL-34 Antibodies

Binding Affinity to Human IL-34

Binding affinity of anti-IL-34 monoclonal antibodies of the present invention to human IL-34 including the leader sequence, or mature human IL-34, may be determined by methods known in the art. Except where noted, all reagents and materials may be purchased from Meso Scale Discovery (MSD®), and measurements may be performed at 37° C. Human and mouse IL-34 can be made and purified using IMAC and size exclusion chromatography or purchased from commercial suppliers. Human CSF1R Fc fusion protein (Exemplified compound D) is also made, purified by MabSelect™ SuRe™ (GE Healthcare), and further polished by size exclusion chromatography.

Briefly, usually a 2-fold or 3-fold dilution series of human, cyno or mouse IL-34 is prepared from a starting concentration of 40, or 50 or 60 or 80 or 100 or 120 nM to 100 fM; and each series includes an IL-34 blank control. Samples are prepared in 3% (w/v) Blocker A solution (MSD®, #R93AA-1) and a fixed final concentration of 5-50 pM of each exemplified antibody in Table 1 is added to each sample. An antibody only control is included. A volume of 50 µl of each protein-antibody sample is added to individual wells of a 96-well microtiter plate (Greiner, EK-20101). The plate is sealed with optical adhesive film (Thermo Fisher Scientific, #4311971) and incubated at 37° C. for 1-3 days to allow for sample equilibrium. On the day before analysis, each row of a 96-well MSD® Standard plate (MSD®, #L15XA) is coated with 30 µl of the corresponding IL-34 (as used in the titration series) at a concentration of 1 µg/ml in phosphate buffered saline (PBS). On the day of the experiment, the MSD® Standard plate is washed three times with 150 µl PBST (PBS with 0.05% Tween) and blocked with 150 µl of 3% Blocker A solution for 60 min at room temperature with shaking at 300 rpm on a MaxQ 4450 benchtop shaker (Thermo Fisher Scientific). Following three washes with PBST, 50 µl of each protein-antibody sample (prepared and incubated as described above) is added to the MSD® Standard plate and incubated for 150 seconds at 37° C. with shaking at 300 rpm. Following three times wash with PBST, 50 µl of 1 µg/ml SULFO-TAG labeled detection antibody prepared in 1% (w/v) Blocker A solution is added to the MSD® Standard plate and the plate is incubated at 37° C. for 150 seconds with shaking at 300 rpm. The plate is washed three more times with PBST followed by the addition of 150 µl/well of 1× Read buffer (MSD®, #R92TC-2). The MSD® Standard plate is read using a MESO Quickplex SQ 120/ 1300 instrument (Meso Scale Discovery). Data analysis is done using GraphPad Prism 8 (Version 8.0.0 for Windows, GraphPad Software, La Jolla Calif. USA, www.graphpad.com) and binding affinity (KD is determined using GraphPad Prism 8's integrated Four Parameter Logistic Curve Model. Results are provided in Table 2, 3 and 4.

TABLE 2

Binding affinity ($K_D$) of antibody-human IL-34 complexes at 37° C.

| Antibody | Binding Affinity, $K_D$ (pM, 37° C., Mean ± STDEV, n = 5) Antigen (mature Human IL-34) |
|---|---|
| Exemplified Antibody 1 | 59 ± 7 |
| Exemplified Antibody 2 | 54 ± 7 |
| Exemplified compound D (hCSF1R-Fc) | 56 ± 12 |

TABLE 3

Binding affinity ($K_D$) of antibody-cyno IL-34 complexes at 37° C.

| Antibody | Binding Affinity, $K_D$ (pM, 37° C., Mean ± STDEV, n = 5) Antigen (Cyno IL-34) |
|---|---|
| Exemplified Antibody 1 | 108 ± 25 |
| Exemplified Antibody 2 | 152 ± 31 |

TABLE 4

Binding affinity ($K_D$) of antibody-mouse IL34 complexes at 37° C.

| Antibody | Binding Affinity, $K_D$ (pM, 37° C.) Antigen (Mouse IL-34) |
|---|---|
| Exemplified Antibody 3 | 16 |

IL-34 binds to human CSF1R at approximately 50-100 pM affinity, necessitating a high-affinity antibody for effective neutralization of this cytokine in the CNS. Blocking IL-34 is believed to provide a useful means for disease modification while avoiding safety concerns associated with some existing immunomodulatory therapies. Therefore, neutralizing IL-34-mediated signaling represents a therapeutic approach for the management of neuroinflammation, microgliosis and neurodegenerative diseases, such as Alzheimer's Disease and other tauopathies and inflammatory diseases.

The results in Tables 2, 3, and 4 show that Antibodies 1, 2, and 3 possess high affinity for IL-34, and in particular, Antibody 1 and Antibody 2 show affinity for human IL-34 comparable to hCSF1R-Fc. Therefore, the Antibodies of the present invention possess binding properties that enable them to effectively neutralize IL-34 in vivo.

Physicochemical Attributes:

With respect to therapeutic antibody product attributes, including Chemical Stability, Photostability, 3× Slow Freeze/Thaw, Solubility, Antibody 1 exhibits a desirable combination of physicochemical attributes for use as a human therapeutic agent.

Stability Sample Preparation

To prepare stability samples, the aqueous antibody solution is dialyzed overnight at 4° C. into PBS, or 10 mM histidine/280 mM mannitol, pH 6 (H6M) or 10 mM histidine/150 mM NaCl, pH 6 (H6N), or 10 mM histidine/17% sucrose, pH 6.0 (H6S). Polysorbate-80 is added to final stability sample at 0.05% ("T") when required. The formulated Antibody 1 is further concentrated to the desired concentration using an Amicon spin concentrator. Abbreviations: 4 wk=4-week; H6MT=10 mM histidine/280 mM mannitol/0.05% polysorbate, pH 6.0; H6ST=10 mM histidine/17% sucrose, 0.05% polysorbate, pH 6.0.

Chemical Stability

Antibody 1 demonstrates an acceptable rating for four weeks (4 wk) chemical stability hotspot check at 5 mg/ml in PBS. After four weeks of storage at 35° C. in PBS and compared to time 0 control, Antibody 1 shows 0.26% aggregate growth, as measured by analytical size exclusion chromatography (aSEC). Hotspots are checked by LC-MS (liquid chromatography-mass spectrometry) peptide mapping. The following degradation/hotspots changes are reported in PBS at 35° C. when compared to 4 wk/4° C. sample: isomerization of D104 (0.1%); cleavage of G93/D94/S95 (0.8%). Total change of CDR degradation was 0.9%.

High Concentration Stability Temperature Hold

Antibody 1 demonstrates an acceptable rating for the 4 wk high concentration stability at 100 mg/ml in H6MT. After 4 wk storage at 35° C. and compared to time 0 control, there is 1.0% aggregate growth, as measured by aSEC, and 0.9% increase in low molecular weight fragments under non-reducing conditions as determined by CE-SDS (capillary electrophoresis sodium dodecyl sulfate). Hotspots are checked by LC-MS peptide mapping. The change of following degradation/hotspots are reported in H6MT after 4 wk incubation at 35° C. and compared to the control of 4 wk incubation at 5° C.: deamidation of Q91 (0.1%); isomerization of D104 (0.1%); cleavage of G93/D94/S95 (0.5%). Total change of CDR degradation was 0.7%.

Solubility

Antibody 1 demonstrates an acceptable rating based on solubility assessment. The antibody achieves 150 mg/ml in both H6M and H6N formulations with no visible precipitation or phase separation observed after 3 days of storage at 5° C. followed by one week of storage at −5° C.

Photostability

Antibody 1 demonstrates an acceptable rating for photostability. Antibody in H6MT at 100 mg/ml is exposed to UV/VIS light (20% ICH guidelines) and compared to dark control sample. Chemical degradation is assessed by LC-MS peptide mapping. Total change in CDR hotspots analysis is 0.1%. Growth of cleavage was observed at residues G93/D94/S95 of light chain was 0.1%. Upon exposure to UV/VIS, the aggregate growth is 3.6% as determined by aSEC.

High Concentration Slow Freeze/Thaw Stability

Physical stability of Antibody 1 is assessed in slow freeze-thaw and demonstrates an acceptable rating when formulated in H6ST. After 3× slow freeze-thaw cycles in a shelf lyophilizer (VirTis SP Scientific), Antibody 1 shows 0.1% aggregate increase in H6ST determined by aSEC when compared to time 0 control.

Example 3: In Vitro Functional Characterization of the Anti-Human IL-34 Antibodies Neutralization of IL-34 In Vitro Antibodies of the present invention are tested for the ability to neutralize IL-34 binding and/or activity. Neutralization of IL-34 binding and/or activity by antibodies of the present invention may be assessed by one or more IL-34/CSF1R receptor binding assay formats, as well as IL-34 cell-based activity assays, for example, as described below.

Screening for neutralizing antibodies of IL-34/CSF1R binding may initially be done through an enzymatic assay. Such assays can use recombinantly expressed CSF1R extracellular domain proteins capable of binding to IL-34. These proteins can be bound to an ELISA plate in order to capture soluble IL-34. IL-34 can then be detected through either biotinylation of the antigen and detection via a streptavidin/neutravidin conjugated peroxidase or phosphatase enzyme. Alternatively, another detection technique may be used, such as an antibody that detects a his-tagged version of IL-34. Such neutralization assays involve pre-incubation of the antibody being assessed with the labeled IL-34 (for example, for 1 hour) before addition to the binding assay (as well as control samples in which no antibody targeting IL-34 is involved). Concentrations of labeled IL-34 near the 50% binding level ($EC_{50}$) may be used, as well as varying concentrations (for example, in assessing a dose response of the antibody such as from about 100 micromolar down to about 1 picomolar). Antibody inhibition assessed for a range allows determination of potency ($IC_{50}$).

Inhibition of IL-34 Induced Responses In Vitro

Neutralization of IL-34 activity by antibodies of the present invention may be assessed by one or more of the IL-34 cell-based assays, for example, as described below. The ability of antibodies of the present invention to neutralize human IL-34 induced luciferase reporter activity can be assessed in NIH-3T3 hCSF1R AP1, or 293 hCSF1R SRE cells, transfected with cDNAs to express human CSF1R, mouse CSF1R or cynomolgus CSF1R (human CSF1R (accession: NP_001275634.1); mouse CSF1R (accession: NM_001037859.2) and cyno CSF1R (accession: NC_022277). (The terms "cyno", "cynomolgus" or "cynomolgus monkey" are used interchangeably, herein.) For example, 293/SRE cells stably overexpressing human CSF1R (hCSF1R) are dissociated in 0.05% trypsin-PBS and plated at 70,000 cells per 100 ml in tissue culture-treated 96 well plates. The following day, growth media is removed, and cells starved with DMEM-F12 (Dulbecco's Modified Eagle Medium: Nutrient Mixture F-12) supplemented with heat-inactivated 1% FBS (fetal bovine serum). 24 hr-post starve, cells are treated with 100 ng/ml human IL-34 or cyno IL-34 and multiple concentrations of either hCSF1R-Fc or Antibody 1 for 6 hr. Following incubation, cells are lysed with 50 ul Promega™ Glo™ Lysis Buffer (Promega™ E266A) for 5 min with gentle agitation. 50 ml of Bright-Glo™ luminescence reagent (Promega™ E2620) is added and incubated on lysed cells for 2 min. Luminescence is read on Perkin Elmer Wallac 1420 Victor2™ Microplate Reader. The reduction in relative fluorescence units (RFUs) shown in Table 5, and FIG. 1, reflects the ability of Antibody 1 to neutralize IL-34 and reduce luciferase activity. The half maximum inhibitory concentration ($IC_{50}$) value for Antibody 1 is 385 pM for neutralization of hIL-34 (FIG. 1), and 654 pM for cyno IL-34. Human CSF1R-Fc is used as a positive control in this assay and inhibits luciferase activity with an $IC_{50}$ of 560 pM.

TABLE 5

Antibody 1 neutralization of human IL-34 induced luciferase reporter activity in hCSF1R expressing 293 SRE cells.

| Concentration [nM] | hCSF1R-Fc | | Antibody 1 | |
|---|---|---|---|---|
| | Average RLU | Standard deviation | Average RLU | Standard deviation |
| 133 | 1216 | 93.3 | 1180 | 18.4 |
| 26.6 | 995 | 153.4 | 1047.5 | 202.9 |
| 5.32 | 962 | 33.2 | 1117.5 | 38.9 |
| 1.064 | 2209 | 292.7 | 1494 | 70.7 |
| 0.213 | 7342.5 | 1282.0 | 7157.5 | 557.9 |
| 0.043 | 8472.5 | 727.6 | 7993 | 229.1 |
| 0.009 | 8185 | 459.6 | 8377.5 | 463.2 |
| 0.002 | 8253 | 365.6 | 8200.5 | 526.8 |
| IC50 [nM] | 95% CI [nM] | | IC50 [nM] | 95% CI [nM] |
| 0.5598 | 0.4047 to 0.7743 | | 0.3852 | 0.3364 to 0.4412 |

Table 5 and FIG. 1 show that Antibody 1 can effectively neutralize human IL-34 induced luciferase reporter activity in the above 293 hCSF1R cell-based assay ($IC_{50}$ 0.3852 nM), and demonstrate potency at least comparable to or better than hCSF1R-Fc in this assay. These data support the ability of Antibody 1 to neutralize human IL-34 mediated signaling and treat diseases in which IL-34 mediated signaling contributes to etiopathogenesis.

Figure 2:
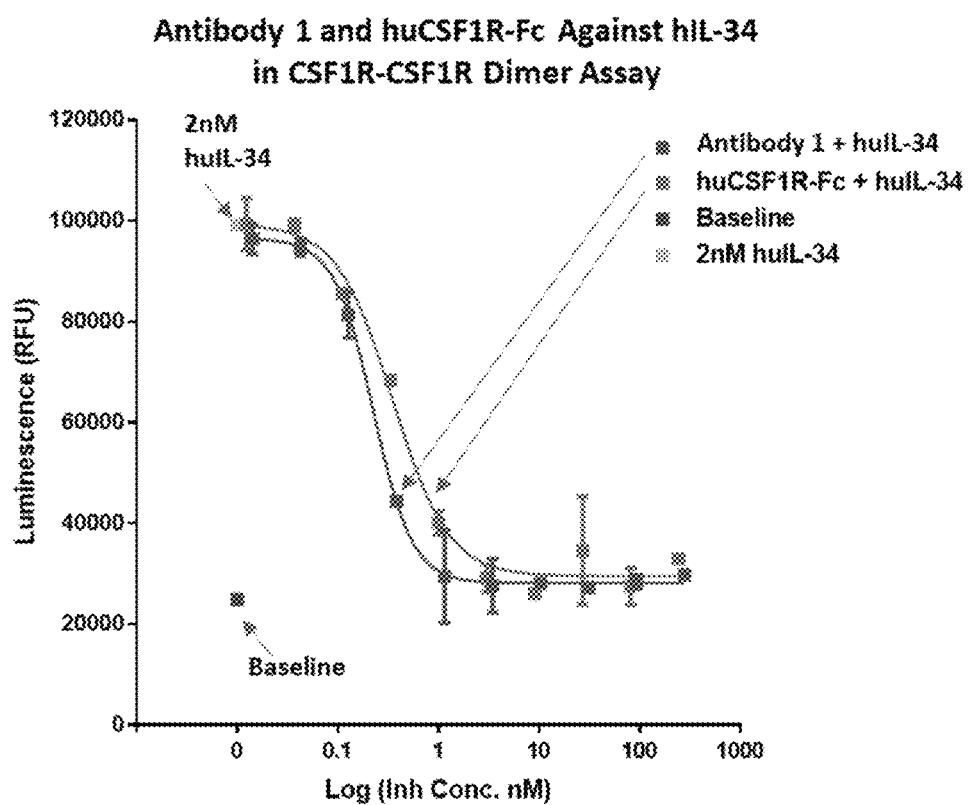
FIG. 2 shows the ability of Antibody 1 to neutralize the dimerization of CSF1R in the PathHunter eXpress Dimerization Assay.

Ability of Antibody 1 to Neutralize the Dimerization of the CSF1R in the PathHunter® eXpress Dimerization Assay:

Human IL-34 neutralization can further be assessed by plating U2OS CSF1R/CSF1R cells (Path Hunter® eXpress Dimerization Assay, DiscoverX) in 96-well plates to assess the ability of anti-IL-34 antibodies to inhibit the dimerization of CSF1R. These assays utilize Enzyme Fragment Complementation (EFC) technology, where the b-galactosidase (b-gal) enzyme is split into two fragments, ProLink (PK) and Enzyme Acceptor (EA). Independently these fragments have no b-gal activity; however, when forced to complement through protein-protein interactions, they form an active b-gal enzyme. The PathHunter® eXpress Dimerization assay detects ligand-induced dimerization of two subunits of the CSF1R receptor-dimer pair. The cells have been engineered to co-express one CSF1R receptor subunit fused to Enzyme Donor (ED), and a second CSF1R dimer partner fused to Enzyme Acceptor (EA). Binding of human IL-34 to one receptor subunit induces it to interact with its dimer partner, forcing complementation of the two enzyme fragments. This results in the formation of a functional enzyme that hydrolyzes a substrate to generate a chemiluminescent signal. The reduction in relative fluorescence units (RFUs) shown in Table 6, and/or FIG. 2, reflects the ability of Antibody 1 to neutralize human IL-34 and reduce chemiluminescence. The half maximum inhibitory concentration ($IC_{50}$) value for Antibody 1 is 226 pM. Human CSF1R-Fc is used as a positive control in this assay and inhibits luciferase activity with an $IC_{50}$ of 353 pM. The data in Table 6 and FIG. 2 support the ability of the Antibody 1 to block the interaction of human IL-34 with CSF1R, thereby inhibiting the dimerization of CSF1R in this assay. This data supports the use of the antibodies of the present invention to neutralize human IL-34.

TABLE 6

Ability of Antibody 1 to neutralize the dimerization of the CSF1R in the PathHunter ® eXpress Dimerization Assay.

| hCSF1R-Fc | | | Antibody 1 | | |
|---|---|---|---|---|---|
| Con [nM] | Avg RLU | Stdev | Con [nM] | Avg RLU | Stdev |
| 0.012 | 99405 | 5235.4 | 0.014 | 96495.5 | 3039.8 |
| 0.037 | 99090 | 1195.0 | 0.043 | 94760 | 1656.0 |
| 0.112 | 85642.5 | 832.3 | 0.128 | 81315.5 | 4488.0 |
| 0.335 | 68380 | 427.1 | 0.384 | 44394 | 91.9 |
| 1.004 | 40124 | 2375.9 | 1.151 | 29459.5 | 9280.7 |
| 3.011 | 29109 | 2643.2 | 3.453 | 27611.5 | 5296.9 |
| 9.033 | 26071.5 | 1119.4 | 10.360 | 28085.5 | 1103.8 |
| 27.100 | 34622.5 | 10704.9 | 31.080 | 27261 | 916.4 |
| 81.301 | 27529.5 | 3655.0 | 93.240 | 28438 | 1299.7 |
| 243.902 | 32958 | 973.0 | 279.720 | 29827 | 319.6 |
| IC50 [nM] | 95% CI [nM] | | IC50 [nM] | 95% CI [nM] | |
| 0.3525 | 0.2595 to 0.4629 | | 0.2256 | 0.1936 to 0.2630 | |

Ability of Anti-IL-34 Antibodies to Inhibit ERK Phosphorylation in NIH-3T3/CSF1R Cells.

Figure 3:
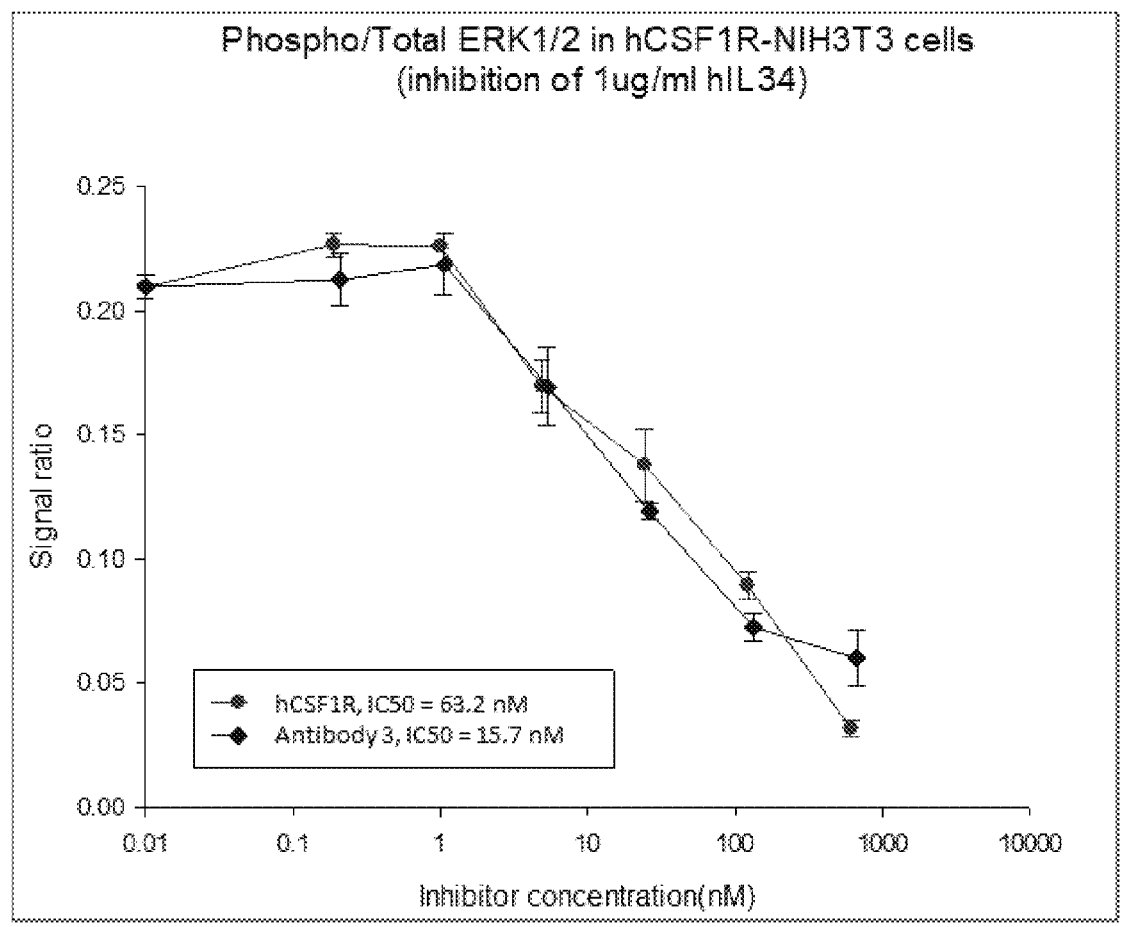
FIG. 3 shows the ability of Antibody 1 to inhibit ERK phosphorylation in NIH-3T3/CSF1R cells.

Alternatively, IL-34 neutralization can be determined by plating NIH-3T3/CSF1R cells in 96 well plates to assess the ability of anti-IL-34 antibodies to inhibit extracellular-signal-regulated kinase (ERK) phosphorylation. In this assay, cells are plated on day 1 in DMEM supplemented with 10% FBS and incubated overnight at 37 C. On day 2, medium is removed, cells are washed in serum-free DMEM and incubated for an additional 24-hour period in serum-free DMEM. On the third day, medium is removed and 1 µg/ml IL-34 is added to the cells for 5 minutes in the presence or absence of anti-IL-34 antibody. Phospho/Total ERK1/2 is assessed by the Whole Cell Lysate Kit (Meso Scale Discovery, cat #K15107D-3). The reduction in relative fluorescence units (RLUs) shown in Table 7 and/or FIG. 3 reflects the ability of Antibody 3 to neutralize IL-34 and reduce chemiluminescence. The half maximum inhibitory concentration ($IC_{50}$) value for Antibody 3 is 16 nM. Human CSF1R-Fc was used as a positive control in this assay and inhibited luciferase activity with an $IC_{50}$ of 63 nM.

TABLE 7

Ability of Antibody 3 to inhibit ERK phosphorylation in NIH-3T3/CSF1R cells.

| CSF1R | | | Antibody 3 | | |
|---|---|---|---|---|---|
| Conc(nM) | RLU | Stdev | Conc(nM) | RLU | Stdev |
| 0 | 0.20982427 | 0.00490388 | 0 | 0.20982427 | 0.00490388 |
| 0.19 | 0.22678655 | 0.00463113 | 0.21 | 0.21266665 | 0.01065081 |
| 1 | 0.22612366 | 0.00094345 | 1.067 | 0.21877016 | 0.01222609 |
| 4.87 | 0.1696282 | 0.01027709 | 5.33 | 0.16963485 | 0.01577903 |
| 24.37 | 0.13803397 | 0.01444251 | 26.27 | 0.11909114 | 0.00324742 |
| 121.84 | 0.08925054 | 0.0052968 | 133.33 | 0.07254438 | 0.00527854 |
| 609.19 | 0.03167946 | 0.00344925 | 666.67 | 0.05997649 | 0.01118308 |
| | $IC_{50}$(nM) | 63.2 | | $IC_{50}$(nM) | 15.7 |

Figure 4:
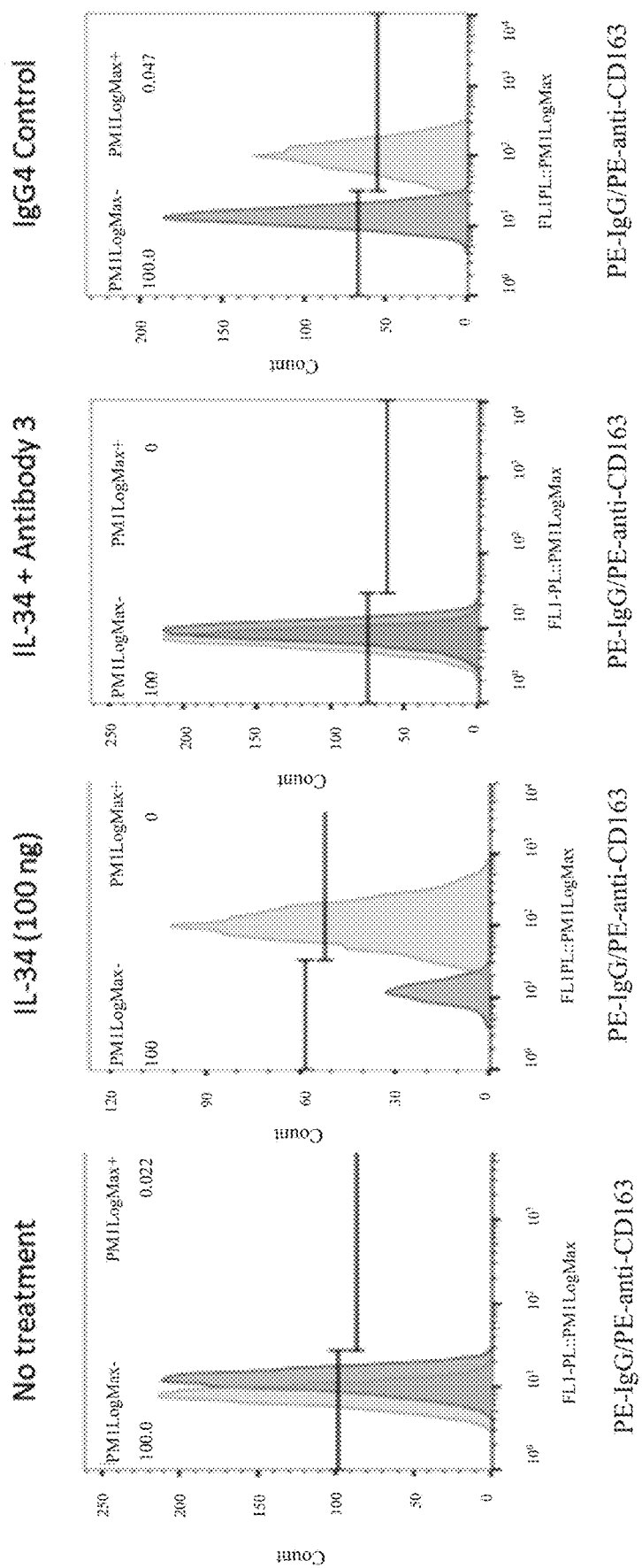
FIG. 4 shows the ability of anti-IL34 antibodies to inhibit IL-34 induced expression of CD163 in human monocytes by flow cytometry.

Ability of Anti-IL34 Antibodies to Inhibit IL-34 Induced Expression of CD163 in Human Monocytes by Flow Cytometry:

IL-34 neutralization can also be assessed by measuring the expression of the cell surface antigen CD163 in human monocytes after treatment with IL-34 by flow cytometry (See for example, Boulakirba, S., et al. *IL-34 and CSF-1 display an equivalent macrophage differentiation ability but a different polarization potential. Sci Rep* 8, 256 (2018). CD14-positive monocytes are treated with IL-34 for 72 hrs and CD163 expression is assessed by flow cytometry after staining with antibodies for CD163. In the experiments described in FIG. 4, a right shift in the number of cells expressing CD163 indicates that IL-34 treatment increases the expression of this antigen in monocytes. The increase in CD163 expression is inhibited by the addition of Antibody 3. An isotype matched IgG4 antibody is used as a negative control in this experiment.

The inhibition by Antibody 3 of CD163 expression in human monocytes, in response to IL-34, demonstrates the ability of the antibodies of the present invention to modulate monocyte/macrophage number and/or phenotypic differentiation responses to IL-34, and supports the use of the present antibodies to treat immune-mediated diseases, such as neuroinflammation and other inflammatory conditions (See, e.g., Lelios, I. et al. *Emerging roles of IL-34 in health and disease*, J Exp Med (2020) 217 (3): e20190290).

Example 4: In Vivo Functional Characterization of the Anti-IL-34 Antibodies

Ability of Antibody 3 to Reduce Microglial Cell Number in Dorsal Cortex and Hippocampus of Mice The ability of anti-IL-34 antibodies of the present invention to reduce microglial cell number is examined using a mouse model. Briefly, FBV female mice (Envigo, 6-8 weeks old) are administered a subcutaneous dose of 50 mg/kg of an Antibody 3, or an isotype matched IgG control antibody. At different times post antibody administration (1, 3, 7 and 14 days), animals are euthanized with $CO_2$ and the brain is perfused with saline. Following perfusion, brain tissue is collected, dorsal cortex and hippocampus are dissected under a microscope and flash frozen in liquid nitrogen.

mRNA is prepared from dorsal cortex and hippocampus and used to assess the impact of anti-IL34 antibody or control antibody treatment on the expression of microglia markers Iba-1 and CD11b by TaqMan. Changes in mRNA expression are normalized versus an internal GAPDH mRNA control and presented as FOLD changes. Expression of Iba-1 and CD11b mRNA is routinely used as a surrogate marker for microglial cell number, and reduction in the expression of these markers is commonly accepted to reflect a reduction in brain microglia. Expression of mRNAs for two of the receptors for IL-34, CSF1R and PTP zeta, and both CSF1R ligands (IL-34 and CSF-1), are also assessed following administration of Antibody 3. Results are provided in Table 8 (A-Hippocampus, and B-Cortex):

TABLE 8

Effect of Antibody 3 on mRNA expression of microglia markers

|  | 1 Day | | 3 Days | | 7 Days | | 14 days | |
|---|---|---|---|---|---|---|---|---|
|  | FOLD | SEM | FOLD | SEM | FOLD | SEM | FOLD | SEM |
| 8A Hippocampus | | | | | | | | |
| Iba1 | 1.16 | 0.15 | 0.91 | 0.06 | 0.50 | 0.02 | 0.74 | 0.04 |
| CD11b | 0.85 | 0.06 | 0.49 | 0.03 | 0.74 | 0.03 | 0.64 | 0.04 |
| CSF-1R | 1.01 | 0.06 | 0.78 | 0.04 | 0.52 | 0.02 | 0.79 | 0.04 |
| PTPRz | 1.01 | 0.00 | 0.98 | 0.00 | 1.00 | 0.00 | 1.00 | 0.00 |
| CSF-1 | 1.01 | 0.03 | 0.79 | 0.05 | 1.11 | 0.05 | 1.03 | 0.05 |
| IL-34 | 1.01 | 0.00 | 0.99 | 0.00 | 0.99 | 0.00 | 0.98 | 0.00 |
| 8B Cortex | | | | | | | | |
| Iba1 | 1.09 | 0.06 | 0.67 | 0.04 | 0.82 | 0.03 | 0.88 | 0.04 |
| CD11b | 0.99 | 0.08 | 0.69 | 0.05 | 0.59 | 0.02 | 0.70 | 0.06 |
| CSF1R | 0.97 | 0.02 | 0.59 | 0.03 | 0.79 | 0.02 | 0.80 | 0.03 |
| PTPRz | 1.01 | 0.00 | 0.98 | 0.00 | 1.00 | 0.00 | 1.00 | 0.00 |
| CSF1 | 1.22 | 0.10 | 1.02 | 0.06 | 0.69 | 0.04 | 0.90 | 0.07 |
| IL34 | 1.01 | 0.00 | 0.99 | 0.00 | 0.99 | 0.00 | 0.98 | 0.00 |

Ability of Antibody 3 to Reduce Microglial Cell Number in a Mouse Model of Alzheimer's Disease (Tg4510 Mouse):

The ability of anti-IL-34 antibodies of the present invention to reduce microglial cell number in a mouse model of Alzheimer's Disease (Tg4510 mouse) is also examined. The Tg4510 mouse is a model of tauopathy characterized by the overexpression of the P301L mutant form of human Tau in the forebrain. These mice are used for studying the formation of neurofibrillary tangles as a model for Alzheimer's disease, neurodegenerative tauopathies and frontotemporal dementia, and they exhibit an age-dependent and region-specific progression of neuropathology associated with cognitive impairment. Briefly, 8-week-old female Tg4510 mice are administered biweekly doses of 5, 15 and 50 mg/kg of an anti-IL-34 antibody, or an isotype-matched IgG control, for 9 consecutive weeks. At the end of the dosing period, animals are euthanized and perfused with PBS. Following perfusion, brain tissue is collected and both hemispheres are separated via a midsagittal section and from each hemisphere, dorsal cortex and hippocampus are dissected under a microscope and flash frozen in liquid nitrogen. To assess the effect of anti-IL-34 antibodies on the expression of microglia markers, mRNA is prepared from hippocampus, and the expression of CD11b, Iba-1, and CSF1R are analyzed by real time PCR, as shown in Table 9 for hippocampus.

TABLE 9

Effect of Antibody 3 on the expression of microglia markers (mRNA from hippocampus, CD11b, Iba-1, and CSF1R, analyzed by real time PCR

|  | CD11b | | Iba1 | | CSF1R | |
|---|---|---|---|---|---|---|
|  | FOLD | SEM | FOLD | SEM | FOLD | SEM |
| Control | 1.00 | 0.03 | 1.00 | 0.07 | 1.00 | 0.07 |
| Antibody 3, 5 mpk | 0.87 | 0.02 | 0.89 | 0.04 | 0.76 | 0.03 |
| Antibody 3, 15 mpk | 0.61 | 0.02 | 0.78 | 0.03 | 0.63 | 0.03 |
| Antibody 3, 50 mpk | 0.36 | 0.01 | 0.65 | 0.02 | 0.45 | 0.02 |

Ability of Anti-IL34 Antibodies to Reduce Phosphorylated Tau in Tg4510 Mice:

To assess whether anti-IL-34 antibodies can reduce phospho-Tau, one of the pathological forms of Tau associated with Alzheimer's Disease, protein lysates are prepared from the cortex of animals treated with anti-IL-34 antibody or IgG control antibody. Briefly, anti-phospho Tau antibodies (AT8) are used to coat the wells of a 96-well plate and incubated for 24 hrs at 4° C. The following day, plates are washed with 0.05% Tween/PBS, blocked with SynBlock™ buffer (ImmunoChemistry Technology) and incubated with cortex lysates for 24 hrs at 4° C. followed by the addition of a biotinylated Tau detection antibody (CP27) and streptavidin-horseradish peroxidase conjugate. As shown in Table 9, treatment with anti-IL-34 antibodies reduced phosphorylated Tau in the cortex of Tg4510 mice.

TABLE 9

FDT248: AT8 Tau ELISA P1 Cortex (μg/mg protein)

|  | mIgG1 Control 50 mg/kg | Antibody 3, 50 mg/kg | Antibody 3, 15 mg/kg | Antibody 3, 5 mg/kg |
|---|---|---|---|---|
| Number of Values | 18 | 17 | 18 | 18 |
| Mean | 997.4 | 492.6 | 531.1 | 890.8 |
| Standard Deviation | 645.4 | 281.7 | 604.1 | 539.5 |
| Standard Error of the mean | 152.1 | 68.3 | 142.4 | 127.2 |
| percent change from control |  | −51% | −17% | −11% |

---

Listing of Amino Acid and Nucleotide Sequences

Heavy Chain of Antibody 1 (SEQ ID NO: 1)
EVQLLESGGGLVQPGGSLRLSCAASGFTFSSYATSWVRQAPGKGLEWVSAISHSG
RSTYYADSVKGRFTISRDNSKNTLYLQMNSLRAEDTAVYYCARGRSSLDTWGQ
GTLVTVSSASTKGPSVFPLAPCSRSTSESTAALGCLVKDYFPEPVTVSWNSGALTS
GVHTFPAVLQSSGLYSLSSVVTVPSSSLGTKTYTCNVDHKPSNTKVDKRVESKYG
PPCPPCPAPEAAGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSL
SLSLG Light Chain of Antibody 1; LC of Antibody 2 (SEQ ID NO: 2)
EIVLTQSPGTLSLSPGERATLSCRASQSISSAYLAWYQQKPGQAPRLLIYASSIRPT
GIPDRFSGSGSGTDFTLTISPLEPEDFAVYYCSQYGDSLSFGGGTKVEIKRTVAAPS
VFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC HCVR of Antibody 1 (SEQ ID NO: 3)
EVQLLESGGGLVQPGGSLRLSCAASGFTFSSYATSWVRQAPGKGLEWVSAISHSG
RSTYYADSVKGRFTISRDNSKNTLYLQMNSLRAEDTAVYYCARGRSSLDTWGQ
GTLVTVSS LCVR of Antibody 1; LCVR of Antibody 2 (SEQ ID NO: 4)
EIVLTQSPGTLSLSPGERATLSCRASQSISSAYLAWYQQKPGQAPRLLIYASSIRPT
GIPDRFSGSGSGTDFTLTISPLEPEDFAVYYCSQYGDSLSFGGGTKVEIK HCDR1 of Antibody 1 (SEQ ID NO: 5)
AASGFTFSSYATS HCDR2 of Antibody 1 (SEQ ID NO: 6)
AISHSGRSTYYADSVKG HCDR3 of Antibody 1 (SEQ ID NO: 7)
ARGRSSLDT LCDR1 of Antibody 1 and Antibody 2 (SEQ ID NO: 8)
RASQSISSAYLA LCDR2 of Antibody 1 and Antibody 2 (SEQ ID NO: 9)
YASSIRPT LCDR3 of Antibody 1 and Antibody 2 (SEQ ID NO: 10)
SQYGDSLS DNA Encoding the Heavy Chain of Antibody 1 (SEQ ID NO: 11)
gaagttcaattgctggagtcaggggggaggattggtccaacccggcgatcccttcggctgtcatgtgctgcttctggatttaccttc
tctagctactacgctacctcctgggtaagacaggcccaggtaaggggctggagtgggtgtcagcaataagtcactccgggcgatct
acatattatgctgattccgtcaaaggacgtttcactataagccgggataatagcaagaacactctgtatctgcaaatgaactctcttc
gggcagaggacaccgctgtttactattgcgctcggggtcgaagctccctcgacacatgggggcagggtacattggtcaccgtat
cctcagcctccaccaagggcccatcggtcttccccgctagcgccctgctccaggagcacctccgagagcacagccgccctggg
ctgcctggtcaaggactacttccccgaaccggtgacggtgtcgtggaactcaggcgccctgaccagcggcgtgcacaccttcc
cggctgtcctacagtcctcaggactctactccctcagcagcgtggtgaccgtgccctccagcagcttgggcacgaagacctaca
cctgcaacgtagatcacaagcccagcaacaccaaggtggacaagagagttgagtccaaatatggtccccatgccacctgc
ccagcacctgaggccgccggggaccatcagtcttcctgttccccccaaaacccaaggacactctcatgatctcccggacccct
gaggtcacgtgcgtggtggtggacgtgagccaggaagaccccgaggtccagttcaactggtacgtggatggcgtggaggtgc
ataatgccaagacaaagccgcgggaggagcagttcaacagcacgtaccgtgtggtcagcgtcctcaccgtcctgcaccagga
ctggctgaacggcaaggagtacaagtgcaaggtctccaacaaaggcctcccgtcctccatcgagaaaaccatctccaaagcca
aagggcagccccgagagccacaggtgtacaccagcccccatcccaggaggagatgaccaagaaccaggtcagcctgacct

| Listing of Amino Acid and Nucleotide Sequences |
|---|

```
gcctggtcaaaggcttctaccccagcgacatcgccgtggagtgggaaagcaatgggcagccggagaacaactacaagaccac
gcctcccgtgctggactccgacggctccttcttcctctacagcaggctaaccgtggacaagagcaggtggcaggaggggaatg
tcttctcatgctccgtgatgcatgaggctctgcacaaccactacacacagaagagcctctccctgtctctgggt
```

DNA Encoding the Light Chain of Antibody 1 (SEQ ID NO: 12)
```
gaaatcgtactgacccaaagcccagggactttgagtttgtccctggggaaagagcaaccctctcatgtcgtgcaagtcaaagta
tatccagtgcatatcttgcttggtatcagcaaaagcctggtcaagcaccaaggctgcttatttatgcctcatctattagacctacaggt
atccctgaccgattctccggaagtggcagtgggactgatttcacacttacaatttccccctggaacctgaagactttgccgtatatt
attgttcacagtatggcgactcacttagtttcggggcggcacaaaggttgaaataaagcggactgtggctgcaccatctgtcttc
atcttccgccatctgatgagcagttgaaatctggaactgcctctgttgtgtgcctgctgaataacttctatcccagagaggccaaa
gtacagtggaaggtggataacgccctccaatcgggtaactcccaggagagtgtcacagagcaggacagcaaggacagcacct
acagcctcagcagccaccctgacgctgagcaaagcagactacgagaaacaaagtctacgcctgcgaagtcacccatcaggg
cctgagctcgcccgtcacaaagagcttcaacaggggagagtgc
```

Heavy Chain of Antibody 2 (SEQ ID NO: 13)
```
EVQLLESGGGLVQPGGSLRLSCAASGFTFFSYAHSWVRQAPGKGLEWVSAISHS
GRSTYYADAVKGRFTISRDNSKNTLYLQMNSLRAEDTAVYYCARGRSSLDTWG
QGTLVTVSSASTKGPSVFPLAPCSRSTSESTAALGCLVKDYFPEPVTVSWNSGALT
SGVHTFPAVLQSSGLYSLSSVVTVPSSSLGTKTYTCNVDHKPSNTKVDKRVESKY
GPPCPPCPAPEAAGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPS
SIEKTISKAKGQPREPQVYTLPPSQEEMTKNQVSLTCLVKGFYPSDIAVEWESNGQ
PENNYKTTPPVLDSDGSFFLYSRLTVDKSRWQEGNVFSCSVMHEALHNHYTQKS
LSLSLG
```

HCVR of Antibody 2 (SEQ ID NO: 14)
```
EVQLLESGGGLVQPGGSLRLSCAASGFTFFSYAHSWVRQAPGKGLEWVSAISHS
GRSTYYADAVKGRFTISRDNSKNTLYLQMNSLRAEDTAVYYCARGRSSLDTWG
QGTLVTVSS
```

HCDR1 of Antibody 2 (SEQ ID NO: 15)
AASGFTFFSYAHS

HCDR2 of Antibody 2 (SEQ ID NO: 16)
AISHSGRSTYYADAVKG

HCDR3 of Antibody 2 (SEQ ID NO: 17)
ARGRSSLDT

DNA Encoding the Heavy Chain of Antibody 2 (SEQ ID NO: 18)
```
gaagttcaattgctggagtcaggggggaggattggtccaaccggcggatccctcggctgtcatgtgctgcttctggatttaccttc
ttcagctacgctcattcctgggtaagacaggcccaggtaagggctggagtgggtgtcagcaataagtcactccgggcgatct
acatattatgctgatgctgtcaaaggacgtttcactataagccgggataatagcaagaacactctgtatctgcaaatgaactctcttc
gggcagaggacaccgctgtttactattgcgctcggggtcgaagctccctcgacacatgggggcagggtacattggtcaccgtat
cctcagcctccaccaagggcccatcggtcttccccgctagcgccctgctccaggagcacctccggagagcacagccgccctggg
ctgcctggtcaaggactacttccccgaaccggtgacggtgtcgtggaactcaggcgccctgaccagcggcgtgcacaccttcc
cggctgtcctacagtcctcaggactctactccctcagcagcgtggtgaccgtgccctccagcagcttgggcacgaagacctaca
cctgcaacgtagatcacaagcccagcaacaccaaggtggacaagagagttgagtccaaatatggtccccatgcccaccctgc
ccagcacctgaggccgccgggggaccatcagtcttcctgttccccccaaaacccaaggacactctcatgatctcccggacccct
gaggtcacgtgcgtggtggtggacgtgagccaggaagaccccgaggtccagttcaactggtacgtggatggcgtggaggtgc
ataatgccaagacaaagccgcgggaggagcagttcaacagcacgtaccgtgtggtcagcgtcctcaccgtcctgcaccagga
ctggctgaacggcaaggagtacaagtgcaaggtctccaacaaggcctcccgtcctccatcgagaaaaccatctccaaagcca
aagggcagccccgagagccacaggtgtacaccctgcccccatcccaggaggagatgaccaagaaccaggtcagcctgacct
gcctggtcaaaggcttctaccccagcgacatcgccgtggagtgggaaagcaatgggcagccggagaacaactacaagaccac
gcctcccgtgctggactccgacggctccttcttcctctacagcaggctaaccgtggacaagagcaggtggcaggaggggaatg
tcttctcatgctccgtgatgcatgaggctctgcacaaccactacacacagaagagcctctccctgtctctgggt
```

Heavy Chain of Antibody 3 (SEQ ID NO: 19)
```
EVQLLESGGGLVQPGGSLRLSCAASGFTFSYYAMSWVRQAPGKGLEWVSAISHR
GGSTLYADSVKGRFTISRDNSKNTLYLQMNSLRAEDTAVYYCARGRSSLDGWG
QGTMVTVSSAKTTPPSVYPLAPGSAAQTNSMVTLGCLVKGYFPEPVTVTWNSGS
LSSGVHTFPAVLQSDLYTLSSSVTVPSSTWPSETVTCNVAHPASSTKVDKKIVPRD
CGCKPCICTVPEVSSVFIFPPKPKDVLTITLTPKVTCVVVDISKDDPEVQFSWFVDD
VEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKSLSHSP
GK
```

Light Chain of Antibody 3 (SEQ ID NO: 20)
```
EIVLTQSPGILSLSPGERASLSCRASTSVSSAYLAWYQQKPGQAPRLLIYASSHRPL
GIPDRFSGSGSGTDFTLTISRLEPEDFAVYYCQQYGDSLSFGGGTKVEIKRADAAP
TVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRNEC
```

HCVR of Antibody 3 (SEQ ID NO: 21)
```
EVQLLESGGGLVQPGGSLRLSCAASGFTFSYYAMSWVRQAPGKGLEWVSAISHR
GGSTLYADSVKGRFTISRDNSKNTLYLQMNSLRAEDTAVYYCARGRSSLDGWG
```

| Listing of Amino Acid and Nucleotide Sequences |
| --- |
| QGTMVTVSSAKTTPPSVYPLAPGSAAQTNSMVTLGCLVKGYFPEPVTVTWNSGS
LSSGVHTFPAVLQSDLYTLSSSVTVPSSTWPSETVTCNVAHPASSTKVDKKIVPRD
CGCKPCICTVPEVSSVPIFPPKPKDVLTITLTPKVTCVVVDISKDDPEVQFSWFVDD
VEVHTAQTQPREEQFNSTFRSVSELPIMHQDWLNGKEFKCRVNSAAFPAPIEKTIS
KTKGRPKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKSLSHSP
GK LCVR of Antibody 3 (SEQ ID NO: 22)
EIVLTQSPGILSLSPGERASLSCRASTSVSSAYLAWYQQKPGQAPRLLIYASSHRPL
GIPDRFSGSGSGTDFTLTISRLEPEDFAVYYCQQYGDSLSFGGGTKVEIKRADAAP
TVSIFPPSSEQLTSGGASVVCFLNNFYPKDINVKWKIDGSERQNGVLNSWTDQDS
KDSTYSMSSTLTLTKDEYERHNSYTCEATHKTSTSPIVKSFNRNEC HCDR1 of Antibody 3 (SEQ ID NO: 23)
AASGFTFSYYAMS HCDR2 of Antibody 3 (SEQ ID NO: 24)
AISHRGGSTLYADSVKG HCDR3 of Antibody 3 (SEQ ID NO: 25)
ARGRSSLDG LCDR1 of Antibody 3 (SEQ ID NO: 26)
RASTSVSSAYLA LCDR2 of Antibody 3 (SEQ ID NO: 27)
YASSHRPL LCDR3 of Antibody 3 (SEQ ID NO: 28)
QQYGDSLS DNA Encoding the Heavy Chain of Antibody 3 (SEQ ID NO: 29)
gaagtccaactcttggagagcggtggaggtctggttcagcctggcggttcactgcggcttagctgtgccgctagtggcttcacttt
cagttattatgccatgtcctgggtacgccaggccccaggcaagggtctggaatgggtgtctgccatttcccacaggggcggctca
acattgtacgctgacagtgttaaaggacgttactataagcaggataactcaaaaaacacattgtatctccagatgaactccttg
cgggcagaagacaccgctgtgtattattgtgctcggggtcgctcctccctcgatggctgggggcaaggaaccatggtcactgta
agctccgccaaaacgacacccccatctgtctatccgctcgcacctggatctgccgcccagaccaacagcatggtgaccctggg
ctgtctggtgaagggctacttccctgagcctgtgacagtgacctggaacagcggctctctgtctagcggcgtgcacacattcctg
ccgtgctgcagagcgacctgtacaccctgagcagcagcgtgaccgtgcctagcagcacatggcctagcgagaccgtgacatg
caacgtggcccaccctgcctcttctaccaaggtggacaagaagatcgtgcccagagactgcggctgcaagccttgcatctgcac
cgtgcctgaggtgagcagcgtgttcatcttcccacccaagcccaaggacgtgctcaccatcaccctcaccccccaaggtcacgtg
tgttgtggtagacatcagcaaggatgatcccgaggtccagttcagctggttttgtagatgatgtggaggtgcacacagctcagacg
caaccccgggaggagcagttcaacagcactttccgctcagtcagtgaacttcccatcatgcaccaggactggctcaatggcaag
gagttcaaatgcagggtcaacagtgcagcttttccctgcccccatcgagaaaaccatctccaaaaccaaaggcagaccgaaggc
tccacaggtgtacaccattccacctcccaaggagcagatggccaaggataaagtcagtctgacctgcatgataacagacttcttc
cctgaagacattactgtggagtggcagtggaatgggcagcagcggagaactacaagaacactcagcccatcatggacacag
atggctcttacttcgtctacagcaagctcaatgtgcagaagagcaactgggaggcaggaaatactttcacctgctctgtgttacatg
agggcctgcacaaccaccactactgagaagagcctctcccactctcctggtaaatagtatttaaatgagtttaaa DNA Encoding the Light Chain of Antibody 3 (SEQ ID NO: 30)
gagatagtactgacccaaagtccgggtatattgtccctcagccctggcgaacagagccagcttagctgtcgggcctccaccagt
gtgtcaagcgcgtacttggcctggtaccaacaaaaaccaggccaagcgcctcgactcctgatatatgcctcctcccaccggccc
cttggaatcccggacagattttccggttcaggctcaggtacagattttaccctcactatatcccgactggagcccgaggacttcgca
gtatattactgccagcagtatggtgactccctctcctttggcggggtactaaggttgaaatcaagcgggctgatcggcgcccca
ctgtatccatcttcccaccatccagtgagcagttaacatctggaggtgctagcgtcgtgtgcttcttgaacaacttctaccccaaaga
catcaatgtcaagtggaagattgatggcagtgaacgacaaaatggcgtcctgaacagttggactgatcaggacagcaaagaca
gcacctacagcatgagcagcaccctcacgttgaccaaggacgagtatgaacgacataacagctatacctgtgaggccactcac
aagacatcaacttcacccattgtcaagagcttcaacaggaatgagtgt Human IL-34 (SEQ ID NO: 41)
NEPLEMWPLTQNEECTVTGFLRDKLQYRSRLQYMKHYFPINYKISVPYEGVFRIA
NVTRLQRAQVSERELRYLWVLVSLSATESVQDVLLEGHPSWKYLQEVETLLLNV
QQGLTDVEVSPKVESVLSLLNAPGPNLKLVRPKALLDNCFRVMELLYCSCCKQS
SVLNWQDCEVPSPQSCSPEPSLQYAATQLYPPPPWSPSSPPHSTGSVRPVRAQGE
GLLP Murine IL-34 (SEQ ID NO: 42)
NENLEIWTLTQDKECDLTGYLRGKLQYKNRLQYMKHYFPINYRIAVPYEGVLRV
ANITRLQKAHVSERELRYLWVLVSLNATESVMDVLLEGHPSWKYLQEVQTLLEN
VQRSLMDVEIGPHVEAVLSLLSTPGLSLKLVRPKALLDNCFRVMELLYCSCCKQS
PILKWQDCELPRLHPHSPGSLMQCTATNVYPLSRQTPTSLPGSPSSSHGSLP IgG4PAA hinge region (SEQ ID NO: 51)
ESKYGPPCPPCP IgG4PAA Fc region (SEQ ID NO: 52) |

| Listing of Amino Acid and Nucleotide Sequences |
|---|
| APEAAGGPSVFLFPPKPKDTLMISRTPEVTCVVVDVSQEDPEVQFNWYVDGVEV<br>HNAKTKPREEQFNSTYRVVSVLTVLHQDWLNGKEYKCKVSNKGLPSSIEKTISK<br>AKGQPREPQVYTLPPSQEEMTKNQVSLTCLVKGFYPSDIAVEWESNGQPENNYK<br>TTPPVLDSDGSFFLYSRLTVDKSRWQEGNVFSCSVMHEALHNHYTQKSLSLSLG |

We claim:

1. An antibody that binds human IL-34 wherein the antibody comprises a heavy chain variable region (VH) and a light chain variable region (VL), wherein the VH comprises heavy chain complementarity determining regions (HCDR) HCDR1, HCDR2, and HCDR3, and the VL comprises light chain complementarity determining regions (LCDR) LCDR1, LCDR2, and LCDR3, wherein the HCDR1 comprises the amino acid sequence of SEQ ID NO: 5, the HCDR2 comprises the amino acid sequence of SEQ ID NO: 6, the HCDR3 comprises the amino acid sequence of SEQ ID NO: 7, the LCDR1 comprises the amino acid sequence of SEQ ID NO: 8, the LCDR2 comprises the amino acid sequence of SEQ ID NO: 9, and the LCDR3 comprises the amino acid sequence of SEQ ID NO: 10.

2. The antibody of claim 1, wherein the VH comprises the amino acid sequence of SEQ ID NO: 3 and the VL comprises the amino acid sequence of SEQ ID NO: 4.

3. The antibody of claim 1, wherein the antibody comprises a heavy chain (HC) comprising the amino acid sequence of SEQ ID NO: 1 and a light chain (LC) comprising the amino acid sequence of SEQ ID NO: 2.

4. An antibody encoded by nucleic acids comprising the nucleotide sequences of SEQ ID NO: 11 and 12, respectively; and produced by a process comprising culturing a cell comprising the nucleic acids under conditions such that the antibody is expressed, and recovering the expressed antibody from the culture medium.

5. A pharmaceutical composition comprising the antibody of claim 1 and a pharmaceutically acceptable excipient, diluent, or carrier.

6. A method of determining the human IL-34 level in a bodily fluid comprising:
   (a) contacting the bodily fluid with an anti-human IL-34 monoclonal antibody or antigen-binding fragment thereof that specifically binds to the human IL-34 consisting of the amino acid sequence of SEQ ID NO: 41; wherein the antibody or antigen-binding fragment thereof comprises: heavy chain complementarity determining regions HCDR1, HCDR2 and HCDR3 comprising the amino acid sequences of SEQ ID NO: 5-7, respectively; and light chain complementarity determining regions LCDR1, LCDR2 and LCDR3 comprising the amino acid sequences of SEQ ID NO: 8-10, respectively;
   (b) optionally, removing any non-specifically bound monoclonal antibody or, antigen-binding fragment thereof, and
   (c) detecting and/or quantifying the amount of monoclonal antibody or antigen-binding fragment thereof, which is specifically bound to the human IL-34.

7. The method of claim 6, wherein said bodily fluid is blood, serum or plasma, or cerebrospinal fluid, and said contacting occurs ex vivo.

* * * * *

UNITED STATES PATENT AND TRADEMARK OFFICE
CERTIFICATE OF CORRECTION

| | |
|---|---|
| PATENT NO. | : 11,649,280 B2 |
| APPLICATION NO. | : 17/238549 |
| DATED | : May 16, 2023 |
| INVENTOR(S) | : Marcio Chedid et al. |

It is certified that error appears in the above-identified patent and that said Letters Patent is hereby corrected as shown below:

On the Title Page

Column 2 (item (56) Other Publications) Line 14:
Delete "CellPress," and insert -- Cell Press, --.

Column 2 (item (56) Other Publications) Line 16:
Delete "Interkeukin-34," and insert -- Interleukin-34, --.

Column 2 (item (57) Abstract) Line 3:
Delete "and or" and insert -- and/or --.

Signed and Sealed this
Twenty-first Day of May, 2024

Katherine Kelly Vidal
*Director of the United States Patent and Trademark Office*

SEQUENCE LISTING

<160> NUMBER OF SEQ ID NOS: 34

<210> SEQ ID NO 1
<211> LENGTH: 442
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Thr Ser Trp Val Arg Gln Ala Pro Gly Lys Gly Leu Glu Trp Val
        35                  40                  45

Ser Ala Ile Ser His Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Leu Asp Thr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
```

```
                290                 295                 300
Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly
                435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ala
                20                  25                  30

Tyr Leu Ala Trp Tyr Gln Gln Lys Pro Gly Gln Ala Pro Arg Leu Leu
            35                  40                  45

Ile Tyr Ala Ser Ser Ile Arg Pro Thr Gly Ile Pro Asp Arg Phe Ser
50                  55                  60

Gly Ser Gly Ser Gly Thr Asp Phe Thr Leu Thr Ile Ser Pro Leu Glu
65                  70                  75                  80

Pro Glu Asp Phe Ala Val Tyr Tyr Cys Ser Gln Tyr Gly Asp Ser Leu
                85                  90                  95

Ser Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

```
<210> SEQ ID NO 3
<211> LENGTH: 116
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Thr Ser Trp Val Arg Gln Ala Pro Gly Lys Gly Leu Glu Trp Val
        35                  40                  45

Ser Ala Ile Ser His Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Leu Asp Thr Trp Gly Gln Gly Thr Leu Val
            100                 105                 110

Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ala
            20                  25                  30

Tyr Leu Ala Trp Tyr Gln Gln Lys Pro Gly Gln Ala Pro Arg Leu Leu
        35                  40                  45

Ile Tyr Ala Ser Ser Ile Arg Pro Thr Gly Ile Pro Asp Arg Phe Ser
    50                  55                  60

Gly Ser Gly Ser Gly Thr Asp Phe Thr Leu Thr Ile Ser Pro Leu Glu
65                  70                  75                  80

Pro Glu Asp Phe Ala Val Tyr Tyr Cys Ser Gln Tyr Gly Asp Ser Leu
                85                  90                  95

Ser Phe Gly Gly Gly Thr Lys Val Glu Ile Lys
            100                 105

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Ala Ala Ser Gly Phe Thr Phe Ser Ser Tyr Ala Thr Ser
1               5                   10
```

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Ala Ile Ser His Ser Gly Arg Ser Thr Tyr Tyr Ala Asp Ser Val Lys
1               5                   10                  15

Gly

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Ala Arg Gly Arg Ser Ser Leu Asp Thr
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Ser Ile Ser Ser Ala Tyr Leu Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Tyr Ala Ser Ser Ile Arg Pro Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ser Gln Tyr Gly Asp Ser Leu Ser
1               5

<210> SEQ ID NO 11
<211> LENGTH: 1326
<212> TYPE: DNA
<213> ORGANISM: Artificial Sequence
<220> FEATURE:
<223> OTHER INFORMATION: Synthetic Construct DNA nucleotide sequence

<400> SEQUENCE: 11
gaagttcaat tgctggagtc aggggggagga ttggtccaac ccggcggatc ccttcggctg    60

```
tcatgtgctg cttctggatt taccttctct agctacgcta cctcctgggt aagacaggcc    120
ccaggtaagg ggctggagtg ggtgtcagca ataagtcact ccgggcgatc tacatattat    180
gctgattccg tcaaaggacg tttcactata agccgggata atagcaagaa cactctgtat    240
ctgcaaatga actctcttcg ggcagaggac accgctgttt actattgcgc tcggggtcga    300
agctccctcg acacatgggg gcagggtaca ttggtcaccg tatcctcagc ctccaccaag    360
ggcccatcgg tcttccccgct agcgccctgc tccaggagca cctccgagag cacagccgcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cgaagaccta cacctgcaac    600
gtagatcaca agcccagcaa caccaaggtg gacaagagag ttgagtccaa atatggtccc    660
ccatgcccac cctgcccagc acctgaggcc gccggggac catcagtctt cctgttcccc    720
ccaaaaccca aggacactct catgatctcc cggaccctg aggtcacgtg cgtggtggtg    780
gacgtgagcc aggaagaccc cgaggtccag ttcaactggt acgtggatgg cgtggaggtg    840
cataatgcca agacaaagcc gcgggaggag cagttcaaca gcacgtaccg tgtggtcagc    900
gtcctcaccg tcctgcacca ggactggctg aacggcaagg agtacaagtg caaggtctcc    960
aacaaaggcc tcccgtcctc catcgagaaa accatctcca aagccaaagg gcagccccga   1020
gagccacagg tgtacaccct gccccatcc aggaggaga tgaccaagaa ccaggtcagc   1080
ctgacctgcc tggtcaaagg cttctacccc agcgacatcg ccgtggagtg ggaaagcaat   1140
gggcagccgg agaacaacta caagaccacg cctcccgtgc tggactccga cggctccttc   1200
ttcctctaca gcaggctaac cgtggacaag agcaggtggc aggagggaa tgtcttctca   1260 tgctccgtga tgcatgaggc tctgcacaac cactacacac agaagagcct ctccctgtct   1320
ctgggt                                                             1326

<210> SEQ ID NO 12
<211> LENGTH: 642
<212> TYPE: DNA
<213> ORGANISM: Artificial Sequence
<220> FEATURE:
<223> OTHER INFORMATION: Synthetic Construct of DNA nucleotide sequence

<400> SEQUENCE: 12
gaaatcgtac tgacccaaag cccagggact ttgagtttgt cccctgggga aagagcaacc     60
ctctcatgtc gtgcaagtca aagtatatcc agtgcatatc ttgcttggta tcagcaaaag    120
cctggtcaag caccaaggct gcttatttat gcctcatcta ttagacctac aggtatccct    180
gaccgattct ccggaagtgg cagtgggact gatttcacac ttacaatttc cccctggaa    240 cctgaagact ttgccgtata ttattgttca cagtatggcg actcacttag tttcggggc    300 ggcacaaagg ttgaaataaa gcggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg    540 ctgagcaaag cagactacga gaaacacaaa gtctacgcct gcgaagtcac ccatcagggc    600
ctgagctcgc ccgtcacaaa gagcttcaac aggggagagt gc                      642

<210> SEQ ID NO 13
```

<211> LENGTH: 442
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala His Ser Trp Val Arg Gln Ala Pro Gly Lys Gly Leu Glu Trp Val
        35                  40                  45

Ser Ala Ile Ser His Ser Gly Arg Ser Thr Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Leu Asp Thr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 14
<211> LENGTH: 116
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala His Ser Trp Val Arg Gln Ala Pro Gly Lys Gly Leu Glu Trp Val
        35                  40                  45

Ser Ala Ile Ser His Ser Gly Arg Ser Thr Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Leu Asp Thr Trp Gly Gln Gly Thr Leu Val
            100                 105                 110

Thr Val Ser Ser
        115

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Ala Ala Ser Gly Phe Thr Phe Ser Tyr Ala His Ser
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Ala Ile Ser His Ser Gly Arg Ser Thr Tyr Tyr Ala Asp Ala Val Lys
1               5                   10                  15

Gly

<210> SEQ ID NO 17
<211> LENGTH: 9
<212> TYPE: PRT

<213> ORGANISM: Artificial Sequence
<220> FEATURE:
<223> OTHER INFORMATION: Synthetic Construct

<400> SEQUENCE: 17

Ala Arg Gly Arg Ser Ser Leu Asp Thr
1               5

<210> SEQ ID NO 18
<211> LENGTH: 1326
<212> TYPE: DNA
<213> ORGANISM: Artificial Sequence
<220> FEATURE:
<223> OTHER INFORMATION: Synthetic Construct nucleotide DNA

<400> SEQUENCE: 18

```
gaagttcaat tgctggagtc agggggagga ttggtccaac ccggcggatc ccttcggctg      60
tcatgtgctg cttctggatt taccttcttc agctacgctc attcctgggt aagacaggcc     120
ccaggtaagg ggctggagtg ggtgtcagca ataagtcact ccggcgatc tacatattat      180
gctgatgctg tcaaaggacg tttcactata agccgggata tagcaagaa cactctgtat      240
ctgcaaatga actctcttcg ggcagaggac accgctgttt actattgcgc tcggggtcga      300
agctccctcg acacatgggg gcagggtaca ttggtcaccg tatcctcagc ctccaccaag     360
ggcccatcgg tcttcccgct agcgccctgc tccaggagca cctccgagag cacagccgcc     420
ctgggctgcc tggtcaagga ctacttcccc gaaccggtga cggtgtcgtg aactcaggc      480
gccctgacca gcggcgtgca caccttcccg gctgtcctac agtcctcagg actctactcc     540
ctcagcagcg tggtgaccgt gccctccagc agcttgggca cgaagaccta cacctgcaac     600
gtagatcaca gcccagcaa caccaaggtg gacaagagag ttgagtccaa atatggtccc      660
ccatgcccac cctgcccagc acctgaggcc gccggggac catcagtctt cctgttcccc      720
ccaaaaccca aggacactct catgatctcc cggacccctg aggtcacgtg cgtggtggtg      780
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca agccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggaaagcaat     1140
gggcagccgg agaacaacta caagaccacg cctcccgtgc tggactccga cggctccttc     1200
ttcctctaca gcaggctaac cgtggacaag agcaggtggc aggaggggaa tgtcttctca     1260
tgctccgtga tgcatgaggc tctgcacaac cactacacac agaagagcct ctccctgtct     1320
ctgggt                                                               1326
```

<210> SEQ ID NO 19
<211> LENGTH: 440
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr

```
            20                  25                  30
Ala Met Ser Trp Val Arg Gln Ala Pro Gly Lys Gly Leu Glu Trp Val
            35                  40                  45

Ser Ala Ile Ser His Arg Gly Gly Ser Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ser Ser Leu Asp Gly Trp Gly Gln Gly Thr Met Val
            100                 105                 110

Thr Val Ser Ser Ala Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
            130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
            195                 200                 205

Val Asp Lys Lys Ile Val Pro Arg Asp Cys Gly Cys Lys Pro Cys Ile
            210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
            275                 280                 285

Phe Asn Ser Thr Phe Arg Ser Val Ser Glu Leu Pro Ile Met His Gln
            290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
            355                 360                 365

Asp Ile Thr Val Glu Trp Gln Trp Asn Gly Gln Pro Ala Glu Asn Tyr
            370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His Thr Glu Lys
            420                 425                 430

Ser Leu Ser His Ser Pro Gly Lys
            435                 440
```

<210> SEQ ID NO 20
<211> LENGTH: 214
<212> TYPE: PRT
<213> ORGANISM: Artificial Sequence
<220> FEATURE:
<223> OTHER INFORMATION: Synthetic Construct

<400> SEQUENCE: 20

```
Glu Ile Val Leu Thr Gln Ser Pro Gly Ile Leu Ser Leu Ser Pro Gly
1               5                   10                  15

Glu Arg Ala Ser Leu Ser Cys Arg Ala Ser Thr Ser Val Ser Ser Ala
            20                  25                  30

Tyr Leu Ala Trp Tyr Gln Gln Lys Pro Gly Gln Ala Pro Arg Leu Leu
        35                  40                  45

Ile Tyr Ala Ser Ser His Arg Pro Leu Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asp Ser Leu
                85                  90                  95

Ser Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210
```

<210> SEQ ID NO 21
<211> LENGTH: 440
<212> TYPE: PRT
<213> ORGANISM: Artificial Sequence
<220> FEATURE:
<223> OTHER INFORMATION: Synthetic Construct

<400> SEQUENCE: 21

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ala Met Ser Trp Val Arg Gln Ala Pro Gly Lys Gly Leu Glu Trp Val
        35                  40                  45

Ser Ala Ile Ser His Arg Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                        85                  90                  95
Ala Arg Gly Arg Ser Ser Leu Asp Gly Trp Gly Gln Gly Thr Met Val
                100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
                180                 185                 190

Ser Glu Thr Val Thr Cys Asn Val Ala His Pro Ala Ser Ser Thr Lys
                195                 200                 205

Val Asp Lys Lys Ile Val Pro Arg Asp Cys Gly Cys Lys Pro Cys Ile
        210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
                260                 265                 270

Asp Asp Val Glu Val His Thr Ala Gln Thr Gln Pro Arg Glu Glu Gln
            275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Lys Glu Gln Met Ala
            340                 345                 350

Lys Asp Lys Val Ser Leu Thr Cys Met Ile Thr Asp Phe Phe Pro Glu
            355                 360                 365

Asp Ile Thr Val Glu Trp Gln Trp Asn Gly Gln Pro Ala Glu Asn Tyr
    370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
            420                 425                 430

Ser Leu Ser His Ser Pro Gly Lys
            435                 440

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Gly Ile Leu Ser Leu Ser Pro Gly
```

```
                1               5              10              15
        Glu Arg Ala Ser Leu Ser Cys Arg Ala Ser Thr Ser Val Ser Ser Ala
                        20                  25                  30

Tyr Leu Ala Trp Tyr Gln Gln Lys Pro Gly Gln Ala Pro Arg Leu Leu
                        35                  40                  45

Ile Tyr Ala Ser Ser His Arg Pro Leu Gly Ile Pro Asp Arg Phe Ser
                    50                  55                  60

Gly Ser Gly Ser Gly Thr Asp Phe Thr Leu Thr Ile Ser Arg Leu Glu
        65                  70                  75                  80

Pro Glu Asp Phe Ala Val Tyr Tyr Cys Gln Gln Tyr Gly Asp Ser Leu
                        85                  90                  95

Ser Phe Gly Gly Gly Thr Lys Val Glu Ile Lys Arg Ala Asp Ala Ala
                        100                 105                 110

Pro Thr Val Ser Ile Phe Pro Pro Ser Ser Glu Gln Leu Thr Ser Gly
                        115                 120                 125

Gly Ala Ser Val Val Cys Phe Leu Asn Asn Phe Tyr Pro Lys Asp Ile
                    130                 135                 140

Asn Val Lys Trp Lys Ile Asp Gly Ser Glu Arg Gln Asn Gly Val Leu
        145                 150                 155                 160

Asn Ser Trp Thr Asp Gln Asp Ser Lys Asp Ser Thr Tyr Ser Met Ser
                        165                 170                 175

Ser Thr Leu Thr Leu Thr Lys Asp Glu Tyr Glu Arg His Asn Ser Tyr
                        180                 185                 190

Thr Cys Glu Ala Thr His Lys Thr Ser Thr Ser Pro Ile Val Lys Ser
                        195                 200                 205

Phe Asn Arg Asn Glu Cys
                    210

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

Ala Ala Ser Gly Phe Thr Phe Ser Tyr Tyr Ala Met Ser
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic Construct

<400> SEQUENCE: 24

Ala Ile Ser His Arg Gly Gly Ser Thr Leu Tyr Ala Asp Ser Val Lys
1               5                   10                  15
Gly

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25
```

Ala Arg Gly Arg Ser Ser Leu Asp Gly
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Arg Ala Ser Thr Ser Val Ser Ser Ala Tyr Leu Ala
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Tyr Ala Ser Ser His Arg Pro Leu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Gln Gln Tyr Gly Asp Ser Leu Ser
1               5

<210> SEQ ID NO 29
<211> LENGTH: 1341
<212> TYPE: DNA
<213> ORGANISM: Artificial Sequence
<220> FEATURE:
<223> OTHER INFORMATION: Synthetic Construct DNA nucleotide

<400> SEQUENCE: 29

| | | | | | |
|---|---|---|---|---|---|
| gaagtccaac | tcttggagag | cggtggaggt | ctggttcagc | ctggcggttc | actgcggctt | 60 |
| agctgtgccg | ctagtggctt | cactttcagt | tattatgcca | tgtcctgggt | acgccaggcc | 120 |
| ccaggcaagg | gtctggaatg | ggtgtctgcc | atttcccaca | ggggcggctc | aacattgtac | 180 |
| gctgacagtg | ttaaaggacg | gtttactata | agcagggata | actcaaaaaa | cacattgtat | 240 |
| ctccagatga | actccttgcg | ggcagaagac | accgctgtgt | attattgtgc | tcggggtcgc | 300 |
| tcctccctcg | atggctgggg | gcaaggaacc | atggtcactg | taagctccgc | caaaacgaca | 360 |
| cccccatctg | tctatccgct | cgcacctgga | tctgccgccc | agaccaacag | catggtgacc | 420 |
| ctgggctgtc | tggtgaaggg | ctacttccct | gagcctgtga | cagtgacctg | aacagcggc | 480 |
| tctctgtcta | gcggcgtgca | cacattccct | gccgtgctgc | agagcgacct | gtacaccctg | 540 |
| agcagcagcg | tgaccgtgcc | tagcagcaca | tggcctagcg | agaccgtgac | atgcaacgtg | 600 |
| gcccacccctg | cctcttctac | caaggtggac | aagaagatcg | tgcccagaga | ctgcggctgc | 660 |
| aagccttgca | tctgcaccgt | gcctgaggtg | agcagcgtgt | tcatcttccc | acccaagccc | 720 |
| aaggacgtgc | tcaccatcac | cctcaccccc | aaggtcacgt | gtgttgtggt | agacatcagc | 780 |
| aaggatgatc | ccgaggtcca | gttcagctgg | tttgtagatg | atgtggaggt | gcacacagct | 840 |

```
cagacgcaac cccgggagga gcagttcaac agcactttcc gctcagtcag tgaacttccc        900
atcatgcacc aggactggct caatggcaag gagttcaaat gcagggtcaa cagtgcagct        960
ttccctgccc ccatcgagaa aaccatctcc aaaaccaaag gcagaccgaa ggctccacag       1020
gtgtacacca ttccacctcc caaggagcag atggccaagg ataaagtcag tctgacctgc       1080
atgataacag acttcttccc tgaagacatt actgtggagt ggcagtggaa tgggcagcca       1140
gcggagaact acaagaacac tcagcccatc atggacacag atggctctta cttcgtctac       1200
agcaagctca atgtgcagaa gagcaactgg gaggcaggaa atactttcac ctgctctgtg       1260
ttacatgagg gcctgcacaa ccaccatact gagaagagcc tctcccactc tcctggtaaa       1320
tagtatttaa atgagtttaa a                                                 1341
```

<210> SEQ ID NO 30
<211> LENGTH: 642
<212> TYPE: DNA
<213> ORGANISM: Artificial Sequence
<220> FEATURE:
<223> OTHER INFORMATION: Synthetic Construct DNA nucleotide

<400> SEQUENCE: 30

```
gagatagtac tgacccaaag tccgggtata ttgtccctca gccctggcga acgagccagc         60
cttagctgtc gggcctccac cagtgtgtca agcgcgtact tggcctggta ccaacaaaaa        120
ccaggccaag cgcctcgact cctgatatat gcctcctccc accggcccct tggaatcccg        180
gacagatttt ccggttcagg ctcaggtaca gattttaccc tcactatatc cgactggag         240 cccgaggact tcgcagtata ttactgccag cagtatggtg actccctctc ctttggcggg        300
ggtactaagg ttgaaatcaa gcgggctgat gcggcgccca ctgtatccat cttcccacca        360
tccagtgagc agttaacatc tggaggtgct agcgtcgtgt gcttcttgaa caacttctac        420
cccaaagaca tcaatgtcaa gtggaagatt gatggcagtg aacgacaaaa tggcgtcctg        480
aacagttgga ctgatcagga cagcaaagac agcacctaca gcatgagcag cacactcacg        540
ttgaccaagg acgagtatga acgacataac agctatacct gtgaggccac tcacaagaca        600
tcaacttcac ccattgtcaa gagcttcaac aggaatgagt gt                           642
```

<210> SEQ ID NO 31
<211> LENGTH: 242
<212> TYPE: PRT
<213> ORGANISM: Human

<400> SEQUENCE: 31

```
Met Pro Arg Gly Phe Thr Trp Leu Arg Tyr Leu Gly Ile Phe Leu Gly
1               5                   10                  15

Val Ala Leu Gly Asn Glu Pro Leu Glu Met Trp Pro Leu Thr Gln Asn
            20                  25                  30

Glu Glu Cys Thr Val Thr Gly Phe Leu Arg Asp Lys Leu Gln Tyr Arg
        35                  40                  45

Ser Arg Leu Gln Tyr Met Lys His Tyr Phe Pro Ile Asn Tyr Lys Ile
    50                  55                  60

Ser Val Pro Tyr Glu Gly Val Phe Arg Ile Ala Asn Val Thr Arg Leu
65                  70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110
```

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
        130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
                180                 185                 190

Val Pro Ser Pro Gln Ser Cys Ser Pro Glu Pro Ser Leu Gln Tyr Ala
            195                 200                 205

Ala Thr Gln Leu Tyr Pro Pro Pro Trp Ser Pro Ser Ser Pro
        210                 215                 220

His Ser Thr Gly Ser Val Arg Pro Val Arg Ala Gln Gly Glu Gly Leu
225                 230                 235                 240

Leu Pro

<210> SEQ ID NO 32
<211> LENGTH: 235
<212> TYPE: PRT
<213> ORGANISM: Mouse

<400> SEQUENCE: 32

Met Pro Trp Gly Leu Ala Trp Leu Tyr Cys Leu Gly Ile Leu Leu Asp
1               5                   10                  15

Val Ala Leu Gly Asn Glu Asn Leu Glu Ile Trp Thr Leu Thr Gln Asp
            20                  25                  30

Lys Glu Cys Asp Leu Thr Gly Tyr Leu Arg Gly Lys Leu Gln Tyr Lys
        35                  40                  45

Asn Arg Leu Gln Tyr Met Lys His Tyr Phe Pro Ile Asn Tyr Arg Ile
50                  55                  60

Ala Val Pro Tyr Glu Gly Val Leu Arg Val Ala Asn Ile Thr Arg Leu
65                  70                  75                  80

Gln Lys Ala His Val Ser Glu Arg Glu Leu Arg Tyr Leu Trp Val Leu
                85                  90                  95

Val Ser Leu Asn Ala Thr Glu Ser Val Met Asp Val Leu Leu Glu Gly
            100                 105                 110

His Pro Ser Trp Lys Tyr Leu Gln Glu Val Gln Thr Leu Leu Glu Asn
            115                 120                 125

Val Gln Arg Ser Leu Met Asp Val Glu Ile Gly Pro His Val Glu Ala
        130                 135                 140

Val Leu Ser Leu Leu Ser Thr Pro Gly Leu Ser Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Pro Ile Leu Lys Trp Gln Asp Cys Glu
                180                 185                 190

Leu Pro Arg Leu His Pro His Ser Pro Gly Ser Leu Met Gln Cys Thr
            195                 200                 205

Ala Thr Asn Val Tyr Pro Leu Ser Arg Gln Thr Pro Thr Ser Leu Pro
        210                 215                 220

Gly Ser Pro Ser Ser Ser His Gly Ser Leu Pro
225                 230                 235

<210> SEQ ID NO 33
<211> LENGTH: 12
<212> TYPE: PRT
<213> ORGANISM: Artificial Sequence
<220> FEATURE:
<223> OTHER INFORMATION: IgG4PAA hinge region

<400> SEQUENCE: 33

Glu Ser Lys Tyr Gly Pro Pro Cys Pro Pro Cys Pro
1               5                   10

<210> SEQ ID NO 34
<211> LENGTH: 216
<212> TYPE: PRT
<213> ORGANISM: Artificial Sequence
<220> FEATURE:
<223> OTHER INFORMATION: IgG4PAA Fc region

<400> SEQUENCE: 34

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
        50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly
    210                 215